United States Patent
Holmberg et al.

(10) Patent No.: US 9,428,746 B2
(45) Date of Patent: Aug. 30, 2016

(54) METHOD AND KIT FOR PURIFYING NUCLEIC ACIDS

(71) Applicant: AKONNI BIOSYSTEMS, INC., Frederick, MD (US)

(72) Inventors: Rebecca Holmberg, Rockville, MD (US); Alissa Erin Gindlesperger, Saint Thomas, PA (US); Tinsley Janna Stokes, Arlington, VA (US); Phillip Belgrader, Severna Park, MD (US)

(73) Assignee: Akonni Biosystems, Inc., Frederick, MD (US)

( * ) Notice: Subject to any disclaimer, the term of this patent is extended or adjusted under 35 U.S.C. 154(b) by 295 days.

(21) Appl. No.: 14/011,267

(22) Filed: Aug. 27, 2013

(65) Prior Publication Data

US 2014/0017672 A1 Jan. 16, 2014

Related U.S. Application Data

(60) Continuation-in-part of application No. 13/682,551, filed on Nov. 20, 2012, now Pat. No. 8,574,923, and (Continued)

(51) Int. Cl.
*C12N 15/10* (2006.01)
*B01L 3/00* (2006.01)
(Continued)

(52) U.S. Cl.
CPC ......... *C12N 15/1017* (2013.01); *B01L 3/5025* (2013.01); *G01N 1/405* (2013.01);
(Continued)

(58) Field of Classification Search
CPC ... G01N 1/405; G01N 1/34; G01N 2030/009
See application file for complete search history.

(56) References Cited

U.S. PATENT DOCUMENTS

| 4,475,821 A | 10/1984 | Koch et al. |
| 4,765,818 A | 8/1988 | Che et al. |

(Continued)

FOREIGN PATENT DOCUMENTS

| EP | 2 174 715 A1 | 4/2010 |
| WO | 00/21973 A1 | 4/2000 |

(Continued)

OTHER PUBLICATIONS

QIAamp Circulating Nucleic Acid Handbook Jan. 2011.*

(Continued)

*Primary Examiner* — Krishnan S Menon
*Assistant Examiner* — Dwan A Gerido
(74) *Attorney, Agent, or Firm* — Michael Ye; Andrews Kurth LLP

(57) ABSTRACT

Methods for automated extraction of nucleic acids are disclosed. Also disclosed are method and kits for isolating fetal nucleic acids from a plasma sample of a pregnant woman. The method includes flowing the plasma sample through a first filter under conditions that allow binding of the fetal and maternal nucleic acids to the first filter; eluting the fetal and maternal nucleic acids bound to the first filter to produce a concentrated nucleic acid sample; flowing the concentrated nucleic acid sample through a second filter under conditions that allow preferential binding of the maternal nucleic acids to the second filter; and recovering the fetal nucleic acid from the concentrated nucleic acid sample that flow through the second filter.

9 Claims, 19 Drawing Sheets

Related U.S. Application Data a division of application No. 12/213,942, filed on Jun. 26, 2008, now abandoned, and a continuation-in-part of application No. 11/933,113, filed on Oct. 31, 2007, now Pat. No. 7,759,112.

(60) Provisional application No. 61/697,116, filed on Sep. 5, 2012, provisional application No. 61/693,963, filed on Aug. 28, 2012.

(51) Int. Cl.
    *G01N 1/40* (2006.01)
    *G01N 33/53* (2006.01)

(52) U.S. Cl.
    CPC ... *G01N33/5308* (2013.01); *B01L 2200/0631* (2013.01); *B01L 2300/0681* (2013.01); *B01L 2300/0832* (2013.01)

(56) References Cited

U.S. PATENT DOCUMENTS

| | | | |
|---|---|---|---|
| 4,810,674 A | 3/1989 | Che et al. | |
| 4,999,164 A | 3/1991 | Puchinger et al. | |
| 5,496,523 A | 3/1996 | Gazit et al. | |
| 5,833,927 A | 11/1998 | Raybuck et al. | |
| 5,876,918 A | 3/1999 | Wainwright et al. | |
| 6,048,457 A | 4/2000 | Kopaciewicz et al. | |
| 6,074,827 A | 6/2000 | Nelson | |
| 6,084,091 A | 7/2000 | Muller | |
| 6,100,084 A | 8/2000 | Miles et al. | |
| 6,200,474 B1 | 3/2001 | Kopaciewicz et al. | |
| 6,268,148 B1 | 7/2001 | Barany et al. | |
| 6,274,371 B1 | 8/2001 | Colpan | |
| 6,337,214 B1 | 1/2002 | Chen | |
| 6,391,541 B1 | 5/2002 | Petersen et al. | |
| 6,431,476 B1 | 8/2002 | Taylor et al. | |
| 6,537,502 B1 | 3/2003 | Shukla et al. | |
| 6,699,713 B2 | 3/2004 | Benett et al. | |
| 6,881,541 B2 | 4/2005 | Petersen et al. | |
| 6,958,392 B2 | 10/2005 | Fomovskaia | |
| 6,987,018 B2 | 1/2006 | Taylor et al. | |
| 7,097,980 B2 | 8/2006 | Barany et al. | |
| 7,157,232 B2 | 1/2007 | Miles et al. | |
| 7,541,166 B2 | 6/2009 | Belgrader et al. | |
| 2003/0032147 A1* | 2/2003 | Sauer | C12N 15/1006 435/91.1 |
| 2003/0194706 A1 | 10/2003 | Brevnov | |
| 2004/0054160 A1* | 3/2004 | Pal | C12Q 1/6806 536/24.3 |
| 2004/0122222 A1 | 6/2004 | Sakurai et al. | |
| 2004/0166589 A1 | 8/2004 | Fisk et al. | |
| 2005/0079535 A1* | 4/2005 | Kirchgesser | C12N 15/1003 435/6.12 |
| 2005/0092685 A1 | 5/2005 | Hilhorst et al. | |
| 2006/0105349 A1 | 5/2006 | Ekenberg et al. | |
| 2006/0124551 A1* | 6/2006 | Gjerde | B01J 20/285 210/656 |
| 2006/0160064 A1 | 7/2006 | Carbonell | |
| 2006/0177352 A1* | 8/2006 | Ziegmann | B01L 3/0275 422/400 |
| 2007/0106071 A1* | 5/2007 | Yamashita | C07H 21/00 536/25.4 |
| 2008/0146789 A1 | 6/2008 | Braman et al. | |
| 2009/0111193 A1 | 4/2009 | Cooney et al. | |
| 2010/0200509 A1 | 8/2010 | Suh et al. | |
| 2011/0130558 A1* | 6/2011 | Ritt | C12N 15/1006 536/25.4 |
| 2012/0164750 A1 | 6/2012 | Gjerde et al. | |

FOREIGN PATENT DOCUMENTS

| | | |
|---|---|---|
| WO | 2009/058414 A1 | 5/2009 |
| WO | 2009/058432 A1 | 5/2009 |

OTHER PUBLICATIONS

Quantitative Analysis of Fetal DNA in Maternal Plasma and Serum: Implications for Noninvasive Prenatal Diagnosis Y.M. Dennis Lo, Mark S.C. Tein, Tze K. Lau, Christopher J. Haines, Tse N. Leung, Priscilla M.K. Poon, James S. Wainscoat, Philip J. Johnson, Allan M.Z. Chang, and N. Magnus Hjelm Am. J. Hum. Genet. 62:768-775, 1998.*

International Search Report and Written Opinion of the International Search Authority mailed Nov. 26, 2013, in International Patent Application No. PCT/US2013/056835 (filed on Aug. 27, 2013).

U.S. Appl. No. 11/933,113, filed Oct. 31, 2007, Patented.
PCT/US2008/056482, Mar. 11, 2008, Pending.
PCT/US2008/068159, Jun. 25, 2008, Pending.
U.S. Appl. No. 12/213,942, filed Jun. 26, 2008, Abandoned.
U.S. Appl. No. 13/682,551, filed Nov. 12, 2012, Patented.
U.S. Appl. No. 14/011,267, filed Aug. 27, 2013, Pending.
PCT/US2013/056835, Aug. 27, 2013, Pending.

Search Report and Written Opinion of the International Search Authority mailed Aug. 25, 2008, in International Patent Application No. PCT/US2008/056482 (filed Mar. 11, 2008).

Search Report and Written Opinion of the International Search Authority mailed Jan. 9, 2009, in International Patent Application No. PCT/US2008/068159 (filed Jun. 25, 2008).

Niederkofler, et al., "Novel Mass Spectrometric Immunoassays for the Rapid Structural Characterization of Plasma Apolipoproteins", Journal of Lipid Research, vol. 44, 2003.

Chandler, et al., "Renewable Microcolumns for Solid-Phase Nucleic Acid Separations and Analysis from Environ. Samples," Trends in Analytical Chemistry, vol. 19, pp. 314-321, 2000.

Whatman Catalog webversion, Mar. 31, 2010, pp. 1 and 2.
File History of U.S. Appl. No. 11/933,113, filed Oct. 31, 2007.
File History of U.S. Appl. No. 12/213,942, filed Jun. 26, 2008.
File History of U.S. Appl. No. 13/682,551, filed Nov. 20, 2012.
Akonni, "TruTip—Breaking the Speed Limit on Ultra-Rapid Nucleic Acid Extraction," Akonni Biosystems, Nov. 16, 2010, pp. 1-8.

Abstract of Chandler, D.P. et al., "Rapid, Simple Influenza RNA Extraction from Nasopharyngeal Samples," Journal of Virological Methods, Mar. 1, 2012, vol. 183, No. 1, pp. 1-2.

Dionne, K. et al., "Extraction of DNA from Mycobacteria Using the Akonni TruTip," Jun. 1, 2012, pp. 1.

"Operating Manual epMotion 5070," Jan. 1, 2008, pp. 1-176.

* cited by examiner

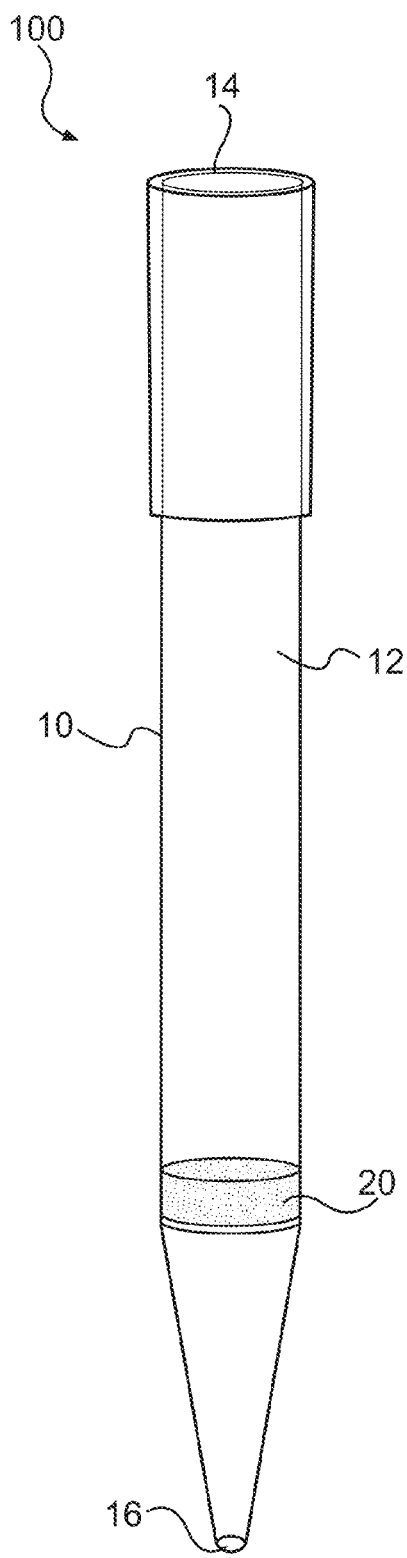
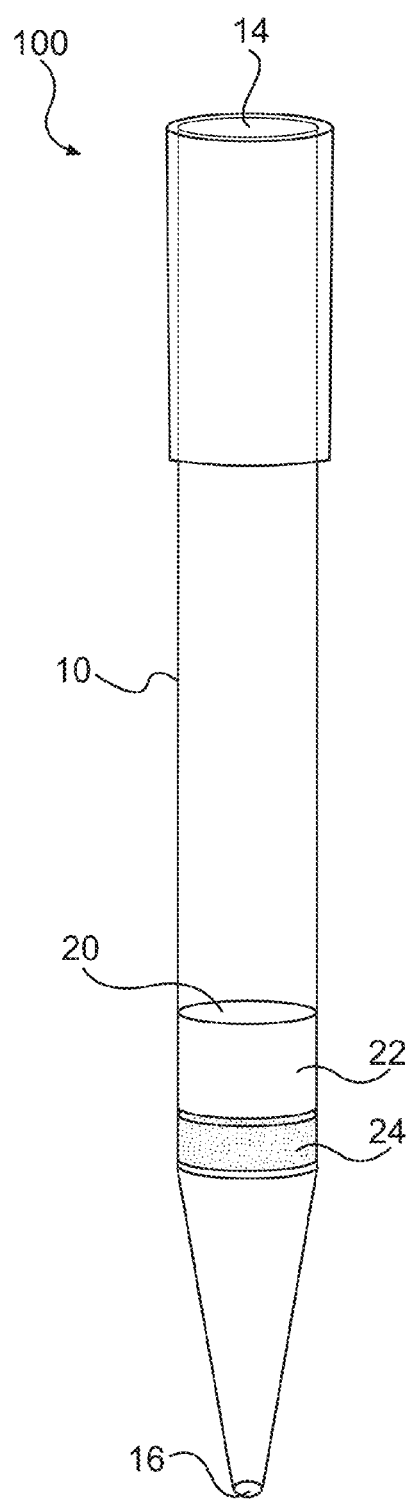
FIG. 1A    FIG. 1B

STEP 1 BIND ACID TO MATRIX

STEP 2 WASH AWAY IMPURITIES

STEP 3 AIR DRY

STEP 4 ELUTE

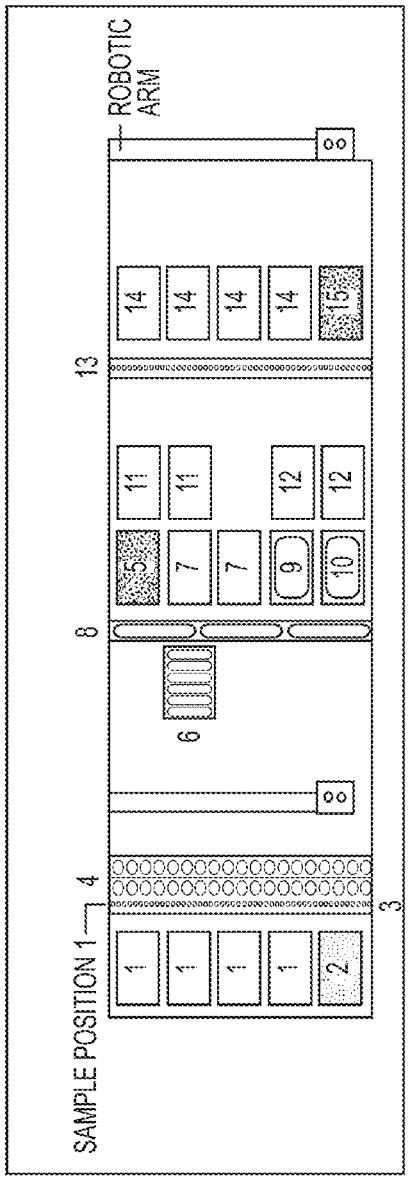
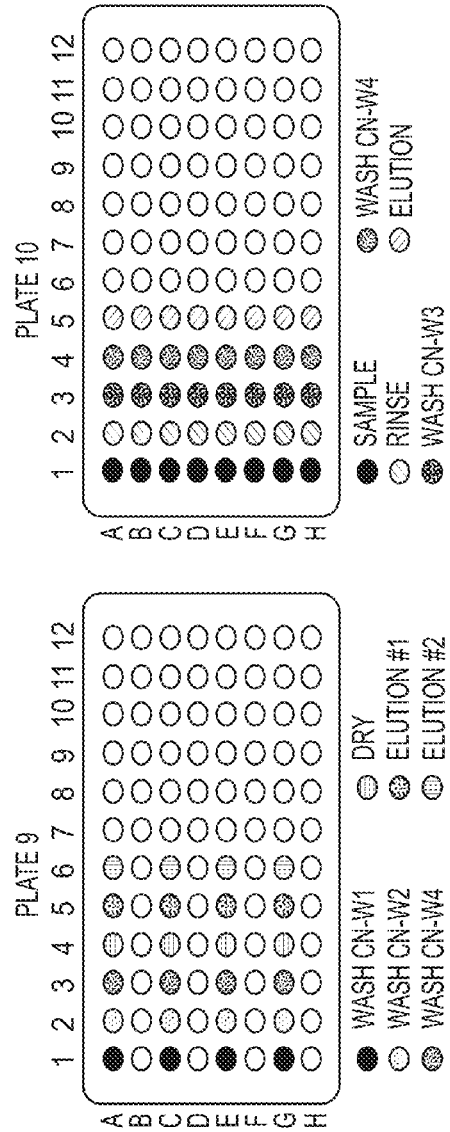
FIG. 10A
FIG. 10B
FIG. 10C

METHOD AND KIT FOR PURIFYING NUCLEIC ACIDS

This application is a continuation-in-part of U.S. patent application Ser. No. 13/682,551, filed on Nov. 20, 2012, which is a divisional of U.S. patent application Ser. No. 12/213,942, filed on Jun. 26, 2008, which is a continuation-in-part of U.S. patent application Ser. No. 11/933,113, filed on Oct. 31, 2007, now U.S. Pat. No. 7,759,112. This application further claims priority to U.S. Provisional Application No. 61/693,963, filed on Aug. 28, 2012 and U.S. Provisional Application No. 61/697,116, filed on Sep. 5, 2012. The entirety of all of the aforementioned applications is incorporated herein by reference.

FIELD

The present invention relates generally to methods for isolating and/or purifying nucleic acids and, in particular, to methods for isolating and/or purifying nucleic acids from a sample using solid monolith filters that are amenable to automation.

BACKGROUND

Nucleic acid purification is necessary for most molecular diagnostics and research use only applications, including purification of fetal DNA for non-invasive prenatal diagnostics (NIPD). The extraction process has been streamlined and automated by utilizing magnetic bead- and membrane-based formats. While effective, particles and membranes have known limitations when confronted with challenging clinical matrices. For example, membranes and bead-based columns are compliant, have small pore sizes, and require some type of support in order to be processed by a centrifuge or vacuum system. The physical characteristics of membranes and bead columns result in significant fluidic resistance, which limits the type of samples that can be efficiently processed without clogging the consumable, and/or the total (input) sample volume that can be uni-directionally processed through the flow path. Conversely, magnetic particles must be distributed throughout the sample by agitation. The need to homogenously distribute magnetic particles within a solution limits the total input sample volume that can be processed with most magnetic bead consumables. Clinical sample attributes (such as viscosity or complexity) can lead to inefficient magnetic particle concentration on the side of a tube or rod. And silica fines can break off of the beads during the extraction process, losing their magnetization and contaminating the final sample.

The high demand for molecular testing for both screening and diagnostic purposes has increased the sample throughput requirements in laboratories. Automation of the processing steps from extraction through detection is paramount to relieve these sample processing burdens. With the inherent limitations of the other extraction technologies mentioned above, there still exists a need for a simple, low cost nucleic acid purification system that is amenable to automation.

SUMMARY

One aspect of the present application relates to an automated method for purifying nucleic acids from a liquid sample, comprising: (a) loading the robotic platform with a plurality of pipette tips, each tip comprising a housing defining a passage way between a first opening and a second opening and a filter occupying a section of the passage way, wherein the filter specifically binds to nucleic acids and wherein the automated robotic platform is capable of automatically dispensing reagents, withdrawing sample contents, and moving pipette tips and/or sample tubes; (b) flowing at least a portion of a liquid sample comprising nucleic acids in through the first opening of a pipette tip such that the nucleic acids pass through the pipette tip and bind to the filter therein; (c) expelling the portion of liquid sample from the pipette tip via the first opening, wherein the portion of liquid sample passes through the filter a second time while exiting the pipette tip; and (d) eluting the nucleic acids from the filter by flowing an elution buffer in through the first opening of the pipette tip and expelling the elution buffer from the pipette tip via the first opening, wherein the elution buffer passes through the filter while entering and exiting the pipette tip.

Another aspect of the present application relates to a method for separating and isolating fetal nucleic acids from maternal nucleic acids in a plasma sample, comprising: (a) flowing a plasma sample comprising fetal nucleic acids and maternal nucleic acids through a first filter under conditions that allow specific binding of the fetal and maternal nucleic acids to the first filter; (b) eluting bound fetal and maternal nucleic acids from the first filter to form a concentrated nucleic acid sample comprising fetal nucleic acids and maternal nucleic acids; (c) flowing the concentrated nucleic acid sample through a second filter under conditions that allow the maternal nucleic acids to bind to the second filter and the fetal nucleic acids to flow through the second filter; and (d) collecting the flow-through fraction from the second filter, wherein the flow-through fraction from the second filter contains fetal nucleic acids.

Another aspect of the present application relates to a kit for isolating fetal nucleic acids from maternal nucleic acids in a plasma sample, comprising: a pipette tip comprising a self-supporting glass frit filter, wherein the glass frit filter has a pore size of 2-220 microns and is not treated or coated with an agent that improves binding of nucleic acid to the glass frit filter, a first binding buffer formulated to be mixed with a plasma sample and provide a first binding mixture having about 17-25% v/v of an aliphatic alcohol and a chaotropic salt at a concentration of between about 0.5 M to about 4.0 M; and a second binding buffer formulated to be mixed with a plasma sample and provide a first binding mixture having about 0-10% v/v of an aliphatic alcohol and a chaotropic salt at a concentration of between about 1 M to about 4.0 M.

These and other aspects and advantages will become apparent when the Description below is read in conjunction with the accompanying Drawings.

BRIEF DESCRIPTION OF THE DRAWINGS

FIGS. 1A-1D are schematics of various embodiments of a pipette tip device comprising a hollow chamber and a filter for purifying nucleic acids in accordance with the present application.

FIG. 6A shows UV-Visible traces from a NanoDrop 1000 (ThermoFisher) from 10 randomly selected replicates of human gDNA extracted from whole blood. FIG. 6B shows a 1% agarose gel of filter tip purified human gDNA extracted from whole blood. M=Fisher 24 kb Max DNA Ladder. Lanes 1-4=~100 ng purified gDNA from four randomly-selected replicates. FIG. 6C shows the reproducibility of gDNA yields from 8 runs each in which 200 µL pooled, whole blood input was processed in accordance with the present invention. FIG. 6D shows that the average gDNA yields from whole blood was linear over a range of whole blood input volumes of 100 µl, 200 µl and 300 µl processed (8 runs each) from 1 ml TruTip® filters (left side) and whole blood volumes of 1000 µl and 2000 µl processed from 5 ml TruTip® filters (center and right). FIG. 6E shows the results a cross-contamination study in which 48 400 µl samples (24 saliva and 24 blank) were subjected to qPCR analysis. FIG. 6F shows UV absorbance results from a comparison of average gDNA yields from 7 individual, blinded saliva samples (Samples A-G; 400 µl input/100 µl elution) extracted using Qiagen's manual spin column method (right column/pairs) and an automated extraction method according to the present invention (left column/pairs). FIG. 6G shows the processing times for 200 µl whole blood processed from a TruTip® filter (Column 1) as compared to five other competitor extraction systems (Columns 2-6).

FIGS. 10A-10C depict a Hamilton STARplus deck layout for purifying DNA from large volume plasma samples (not to scale). The system is equipped with 8×5 ml channels and 8×1 ml channels. Deck Position 1=Hamilton 4 ml filtered tips; 2=Akonni/Hamilton 5 ml filter tips; 3=source plasma samples; 4=50 ml conical tubes; 5=120 ml reagent troughs containing CN-W1, CN-W2 and CN-W4 reagents; 6=low-volume reagent troughs containing proteinase K, CN-B2, CN-B3, EBA2, EBB and CN-W3 reagents; 7=290 ml reagent trough containing CN-L1 reagent; 8=290 ml reagent trough containing CN-B1 reagent; 9=96 deep well plates for Step 1; 10=96 deep well plates for Step 2; 11=sample carriers for purified, final product; 12=Hamilton 1 ml unfiltered tips; 13=Akonni/Hamilton 1 ml LPT 4 mm filter tips.

DETAILED DESCRIPTION

Figure 1C:
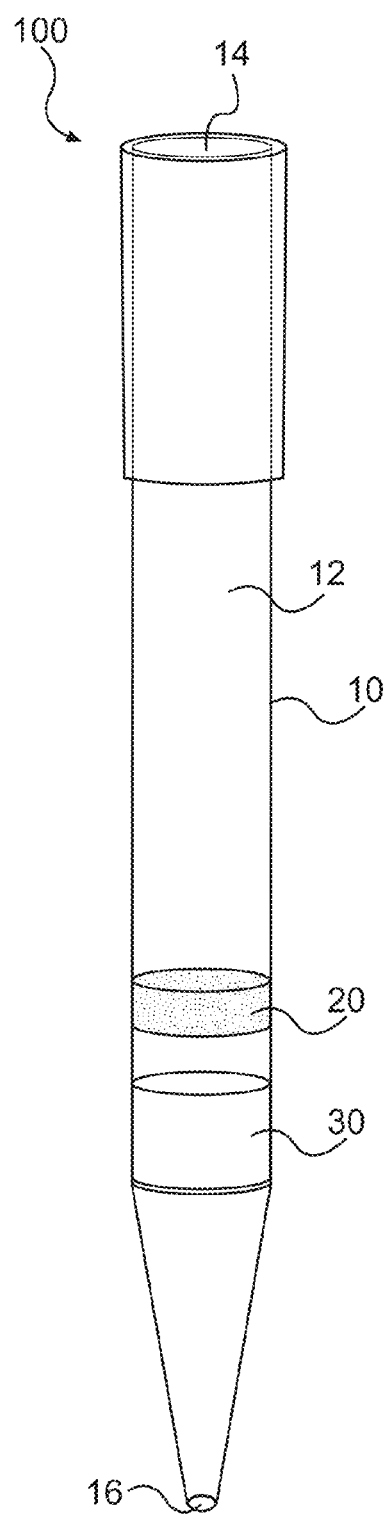

The present application provides methods and devices for purifying nucleic acids from a test sample. Specifically, the present application provides a simple nucleic acid extraction technology whereby a monolithic nucleic acid binding matrix is inserted into a pipette tip or a similar device. Nucleic acid extraction is performed using a sample preparation format that is compatible with most liquid handling instruments and is, therefore, amenable to automation and adaptable to many medium to high-throughput clinical applications and sample matrices. In some embodiments, the present application relates to an automated method for purifying nucleic acids from a liquid sample using a robotic platform with a plurality of pipette tips.

The present application further provides a methodology adaptable for preferential selection for low-molecular weight (LMW) DNA fragments (such as fetal DNA) from a background of higher molecular weight (HMW) DNA (such as maternal DNA). The methodology increases the percentage of LMW DNA present in the sample regardless of the amount of HMW DNA present and provides the ability to process large sample volumes, e.g., up to 20 ml, so as to meet the sensitivity requirement for certain clinical applications. In some embodiments, the present application relates to a method for separating and isolating fetal nucleic acids from maternal nucleic acids in a plasma sample using filter(s) that allow specific binding of the fetal and/or maternal nucleic acids to the filter(s). The present application also provides kit for isolating fetal nucleic acids from maternal nucleic acids in a plasma sample.

As used herein the term "test sample" or "sample" refers to any material that may contain nucleic acid. Examples of the test samples include, but are not limited to, biological samples, environmental samples and non-nature samples. Examples of biological samples include, but are not limited to, tissue samples, biological fluid samples, cell samples, bacterial samples, and virus samples. Tissue samples include tissues isolated from any animal or plant. Biological fluid samples include, but are not limited to, blood, plasma, urine, saliva, sputum, cerebrospinal fluid, nasopharyngeal, buccal, lavages (e.g. bronchial), and leukophoresis samples. Cell samples include, but are not limited to, cultured cells or cells isolated from any sources. Virus samples include, but are not limited to, cultured viruses or isolated viruses. Environmental samples include, but are not limited to, air samples, water samples, soil samples, rock samples and any other samples obtained from a natural environment. The artificial samples include any sample that does not exist in a natural environment. Examples of "artificial samples" include, but are not limited to, purified or isolated materials, cultured materials, synthesized materials and any other man-made materials. In some embodiments, the test samples include sputum, NALC-treated sputum, whole blood or blood culture, plasma, cerebral spinal fluid, nasopharyngeal swab and aspirates, bronchial lavage, fresh or frozen cells and tissues, FFPE samples, buffy coat, blood card, saliva, buccal swab, stool, solid or liquid bacterial cultures, NPA, recreational water and soil.

As used herein, "nucleic acids" refer to individual nucleic acids and polymeric chains of nucleic acids, including DNA and RNA, whether naturally occurring or artificially synthesized (including analogs thereof), or modifications thereof, especially those modifications known to occur in nature, having any length. Examples of nucleic acid lengths that are in accord with the present application include, without limitation, lengths suitable for PCR products (e.g., about 30 to 3000 base pairs (bp), about 30-2000 bp, about 30-1000 bp), DNA fragments in the length range of 50-600 bp, DNA fragments in the length range of 100-350 bp, and human genomic DNA (e.g., on an order from about tens of kilobase pairs (Kb) to gigabase pairs (Gb)). Thus, it will be appreciated that the term "nucleic acid" encompasses single nucleic acids as well as stretches of nucleotides, nucleosides, natural or artificial, and combinations thereof, in small fragments, e.g., expressed sequence tags or genetic fragments, as well as larger chains as exemplified by genomic material including individual genes and even whole chromosomes. As used herein, the term "low-molecular weight (LMW) DNA," refers to DNA fragments having a length of less than about 20 kb, 15 kb, 10 kb, 5 kb, 3 kb, 2 kb, 1 kb, 900 bp, 800 bp, 700 bp, 600 bp, 500 bp, 4000 bp, 350 bp or 300 bp in various embodiments. As used herein, the term "high-molecular weight (HMW) DNA" refers to DNA fragments having a length of greater than about 300 bp, 350 bp, 400 bp, 500 bp, 600 bp, 700 bp, 800 bp, 900 bp, 1 kb, 2 kb, 3 kb, 5 kb, 10 kb, 15 kb, 20 kb, 50 kb, or 100 kb in various embodiments. In some embodiments, the term "high-molecular weight DNA" refers to DNA in the size range of 3000 bp or greater, 2000 bp or greater, 1000 bp or greater, 800 bp or greater, 600 bp or greater, 500 bp or greater, 400 bp or greater, or 350 bp or greater; while the term "low-molecular weight DNA" refers to DNA in the size range of 3000 bp or smaller, 2000 bp or smaller, 1000 bp or smaller, 800 bp or smaller, 600 bp or smaller, 500 bp or smaller, 400 bp or smaller, 350 bp or smaller, or 300 bp or smaller. In some embodiments, the term low-molecular weight DNA refers to fetal DNA present in the mother's circulation (e.g., blood) while the term high-molecular weight DNA refers to maternal DNA.

The terms "monolith adsorbent" or "monolithic adsorbent material," as used herein, refers to a porous, three-dimensional adsorbent material having a continuous interconnected pore structure in a single piece, which may comprise a rigid, self-supporting substantially monolithic structure. A monolith is prepared, for example, by casting, sintering or polymerizing precursors into a mold of a desired shape. The term "monolith adsorbent" or "monolithic adsorbent material" is meant to be distinguished from a collection of individual adsorbent particles packed into a bed formation or embedded into a porous matrix, in which the end product comprises individual adsorbent particles. The term "monolith adsorbent" or "monolithic adsorbent material" is also meant to be distinguished from a collection of adsorbent fibers or fibers coated with an adsorbent, such as filter papers or filter papers coated with an adsorbent.

Filters and Pipette Tips

The filter tip system of the present invention provides a nucleic acid extraction technology whereby a monolithic binding matrix filter is inserted into a pipette tip. The porous monolithic material binds specifically to nucleic acids and is composed of a rigid, self-supporting, substantially monolithic structure. In some embodiments, the porous monolithic material does not include additional materials that provide nucleic acid affinity. In some preferred embodiments, the porous monolithic material is a glass-based monolithic material such as a glass frit. In some embodiments, the glass frit is a sintered glass frit. The porosity of the porous monolithic material, such as a glass frit or sintered glass frit, is application dependent. In general, the porous monolithic material should have a porosity that allows for a desired sample flow rate for a particular application and is capable of retaining nucleic acids in a desired size range. In some embodiments, the porous monolithic material is a glass frit or sintered glass frit having a porosity (i.e., an average pore size) in the range of 2-400 micron, 2-300 micron, 2-220 micron, 2-200 micron, 2-180 micron, 2-160 micron, 2-140 micro, 2-120 micro, 2-100 micron, 2-80 micron, 2-60 micron, 2-40 micron, 2-20 micron, 2-16 micron, 2-10 micron, 2-5.5 micron, 4-400 micron, 4-300 micron, 4-220 micron, 4-200 micron, 4-180 micron, 4-160 micron, 4-140 micro, 4-120 micro, 4-100 micron, 4-80 micron, 4-60 micron, 4-40 micron, 4-20 micron, 4-16 micron, 4-10 micron, 4-5.5 micron, 10-400 micron, 10-300 micron, 10-220 micron, 10-200 micron, 10-180 micron, 10-160 micron, 10-140 micro, 10-120 micro, 10-100 micron, 10-80 micron, 10-60 micron, 10-40 micron, 10-20 micron, 10-16 micron, 16-400 micron, 16-300 micron, 16-220 micron, 16-200 micron, 16-180 micron, 16-160 micron, 16-140 micro, 16-120 micro, 16-100 micron, 16-80 micron, 16-60 micron, 16-40 micron, 40-400 micron, 40-300 micron, 40-220 micron, 40-200 micron, 40-180 micron, 40-160 micron, 40-140 micro, 40-120 micro, 40-100 micron, 40-80 micron, 40-60 micron, 100-400 micron, 100-300 micron, 100-220 micron, 100-200 micron, 100-180 micron, 100-160 micron, 100-140 micro, 100-120 micro, 160-400 micron, 160-300 micron, 160-220 micron, 160-200 micron, 160-180 micron, 200-400 micron, 200-300 micron, or 200-220 micron. In other embodiments, the porous monolithic material is a glass frit or sintered glass frit having two sections of different porosity. Each section may have a porosity in a range described above (e.g. a 4-10 micron section and a 16-40 micron section, or a 16-40 micron section and a 100-160 micron section).

In some embodiments, the filter has a thickness in the range of 1-30 mm, 1-25 mm, 1-20 mm, 1-15 mm, 1-10 mm, 1-8 mm, 1-6 mm, 1-4 mm, 2-30 mm, 2-25 mm, 2-20 mm, 2-15 mm, 2-10 mm, 2-8 mm, 2-6 mm, 2-4 mm, 4-30 mm, 4-25 mm, 4-20 mm, 4-15 mm, 4-10 mm, 4-8 mm, 4-6 mm, 6-30 mm, 6-25 mm, 6-20 mm, 6-15 mm, 6-10 mm, 6-8 mm, 8-30 mm, 8-25 mm, 8-20 mm, 8-15 mm, 8-10 mm, 10-30 mm, 10-25 mm, 10-20 mm, 10-15 mm, 15-30 mm, 15-25 mm, 15-20 mm, 20-30 mm, 20-25 mm, or 25-30 mm.

In some embodiments, the porous monolithic material may be modified with one or more materials having nucleic acid affinity.

In some embodiments, the filter is made of a porous glass monolith, a porous glass-ceramic, or porous monolithic polymers. In some embodiments, the porous glass monolith is produced using the sol-gel methods described in U.S. Pat. Nos. 4,810,674 and 4,765,818, which are hereby incorporated by reference. Porous glass-ceramic may be produced by controlled crystallization of a porous glass monolith. In preferred embodiments, the a porous glass monolith, porous glass-ceramic, or porous monolithic polymer is not coated or embedded with any additional materials, such as polynucleotides or antibodies, to improve its affinity to nucleic acids.

Porous monolithic polymers are a new category of materials developed during the last decade. In contrast to polymers composed of very small beads, a monolith is a single, continuous piece of a polymer prepared using a simple molding process.

In some preferred embodiments, the filter is made of a finely porous glass frit through which a liquid sample may pass. The porous glass frit is not coated or embedded with any additional materials, such as polynucleotides or antibodies, to improve its affinity to nucleic acids. Suitable substrates for purifying nucleic acids include porous glass frits made of sintered glass, which are formed by crushing beads in a hot press to form a single monolithic structure. The uniform structure of the frit provides predictable liquid flow inside the frit and allows the eluent to have similar fluid dynamics as the sample flow. The predictable liquid flow provides high recovery during the elution process.

In some embodiments, the filter is placed in a pipette tip. The filter may also be fitted into columns, syringes or other housing of different volumes and shapes. The method described herein can be carried out using various devices, including manual or automatic pipette, syringe pumps, hand-held syringes, or other type of automated or manual methods for moving liquid across the filter.

In some embodiments, the filter is designed to separate substantially the nucleic acids from extraneous matter in a sample. As used herein "extraneous matter" refers to all materials that are distinct from the nucleic acids in the sample. Examples of such extraneous materials include, but are not limited to, proteins, starches, lipids, metal ions, and larger cellular structures such as membrane fragments and other cellular matters. The phrase "separate substantially" as used herein refers to separations that, in some embodiments, provide the nucleic acids in at least 30% purity with respect to the extraneous materials, in more specific embodiments provide the nucleic acids in at least 50% or 60% purity with respect to the extraneous materials, in still more specific embodiments provide the nucleic acids in at least 70% or 80% purity with respect to the extraneous materials, in yet more specific embodiments provide the nucleic acids in at least 90% or 95% purity with respect to the extraneous materials, and in still yet more specific embodiments, provide the nucleic acids in at least 97% or 99% purity with respect to the extraneous materials. As used herein, nucleic acids in at least 30% purity with respect to the extraneous materials means a nucleic acids preparation in which the nucleic acids-to-extraneous materials weight ratio is 30:70 or higher. Similarly, nucleic acids in at least 99% purity with respect to the extraneous materials means a nucleic acids preparation in which the nucleic acids-to-extraneous materials weight ratio is 99:1 or higher Referring now to FIG. 1A, an embodiment of a pipette tip device 100 includes a housing 10 and a monolithic porous filter 20 that is capable of substantially removing nucleic acids from a liquid containing such nucleic acids. In some embodiments, the filter 20 is a glass frit or sintered glass frit having a uniform porosity. In other embodiments, the filter 20 is a glass frit or sintered glass frit having two sections of different porosity, wherein the section having the larger pore size is disposed closer to the pipette inlet than the section having the smaller pore size. In all these embodiments, the glass frit is not coated or embedded with any additional materials, such as polynucleotides or antibodies, to improve its affinity to nucleic acids.

The pipette tip 100 comprises a pipette tip inlet or opening 16 for flowing nucleic acid materials from a sample source therethrough. The housing 10 is defined by a hollow chamber 12 between a distal opening 14 adopted to receive a pipetting device and the inlet 16. The shape and size of the housing 10 are not particularly limited. The preferred housing configuration is substantially cylindrical so that the flow vectors during operation are substantially straight, thereby minimizing or avoiding dilutional washing that might occur with non-cylindrical configurations. In some embodiments, the housing 10 has a volume of about 0.1 µl to about 50 ml, about 10 µl to about 50 ml, about 100 µl to about 50 ml, about 1 ml to about 50 ml, about 2 ml to about 50 ml, about 5 ml to about 50 ml, about 10 ml to about 50 ml, about 20 ml to about 50 ml, about 0.1 µl to about 20 ml, about 10 µl to about 20 ml, about 100 µl to about 20 ml, about 1 ml to about 20 ml, about 2 ml to about 20 ml, about 5 ml to about 20 ml, about 10 ml to about 20 ml, about 0.1 µl to about 10 ml, about 10 µl to about 10 ml, about 100 µl to about 10 ml, about 1 ml to about 10 ml, about 2 ml to about 10 ml, about 0.1 µl to about 5 ml, about 10 µl to about 5 ml, about 100 µl to about 5 ml, about 1 ml to about 5 ml, about 0.1 µl to about 2 ml, about 10 µl to about 2 ml, about 100 µl to about 2 ml, about 1 ml to about 2 ml, about 0.1 µl to about 1 ml, about 10 µl to about 1 ml, about 100 µl to about 1 ml, about 0.1 µl to about 100 µl or about 10 µl to about 100 µl. In other embodiments, the housing 10 has a volume of about 0.1 ml, about 0.2 ml, about 0.5 ml, about 1 ml, about 2 ml, about 5 ml, about 10 ml, about 20 ml, about 30 ml, about 40 ml or about 50 ml. As used hereinafter, the volume of the housing 10 is also refers to as "tip volume."

Suitable materials for the housing 10 are not particularly limited, and include plastics (such as polyethylene, polypropylene, and polystyrene), glass and stainless steel.

The sample filter 20 may be placed at any position within the housing 10. In some embodiments, the sample filter 20 is placed in the close proximity of the inlet 16 so that samples are filtered immediately after being taken into the housing 10 through the inlet 16. In one embodiment, the sample filter 20 is contiguous with the inlet 16. In another embodiment, the sample filter 20 is separated from the inlet 16 by a distance of 0-60 mm, 0-40 mm, 0-30 mm, 0-20 mm, 0-10 mm, 5-60 mm, 5-40 mm, 5-30 mm, 5-20 mm, 5-10 mm, 10-60 mm, 10-40 mm, 10-30 mm, 10-20 mm, 20-60 mm, 20-40 mm, 20-30 mm, 30-60 mm or 40-60 mm. In other embodiments, the sample filter 20 is separated from the inlet 16 by a distance of 60-120 mm, 60-100 mm, 60-80 mm, 80-120 mm, 80-100 mm or 100-120 mm. In yet other embodiments, the sample filter 20 is separated from the inlet 16 by a distance of 60-80 mm, e.g., about 75 mm. The sample filter 20 may have a porosity suitable for the isolation of nucleic acids of interests. In some embodiments, the sample filter 20 has an average pore size of 4-5.5 micron, 4-16 micron, 16-40 micron, 40-100 micron, 100-160 micron or 2-220 micron.

In some embodiments, the filter 20 comprises two or more subfilters. FIG. 1B shows an embodiment of a pipette tip 100 having a filter 20 comprising subfilters 22 and 24. In some embodiments, the subfilters 22 and 24 have different porosity and are placed in tandem with a space between the subfilters. In other embodiments, subfilters 22 and 24 are placed next to each other without any space between the subfilters (FIG. 1B). In yet other embodiments, the subfilters 22 and 24 are fused to each other to form a monolithic structure 20 having two sections (22 and 24) of different porosity. Typically, the filter or filter section having larger pore sizes is disposed closer to the pipette tip inlet 16. It is believed that arranging the larger pore sized filter nearer the pipette tip inlet helps provide a pre-filter to avoid clogging of the smaller pores with the sample material.

In some embodiments, the subfilter 22 has a pore size of about 80-200 microns, preferably 100-160 micron and the subfilter 24 has a pore size of about 8-80 micron, preferably 16-40 micron. In some embodiments, the subfilter 22 has a pore size of about 8-80 micron, preferably 16-40 micron and the subfilter 24 has a pore size of about 2-16 micron, 4-10 micron or 4.5.5 micron.

In one embodiment, the filter 20 has a thickness between about 1 mm and about 20 mm. In another embodiment, the filter 20 has a thickness between about 2 mm and about 10 mm. In another embodiment, the filter 20 has a thickness between about 2 mm and about 6 mm. In yet another embodiment, the filter 20 has a thickness of about 4 mm.

Figure 1D:
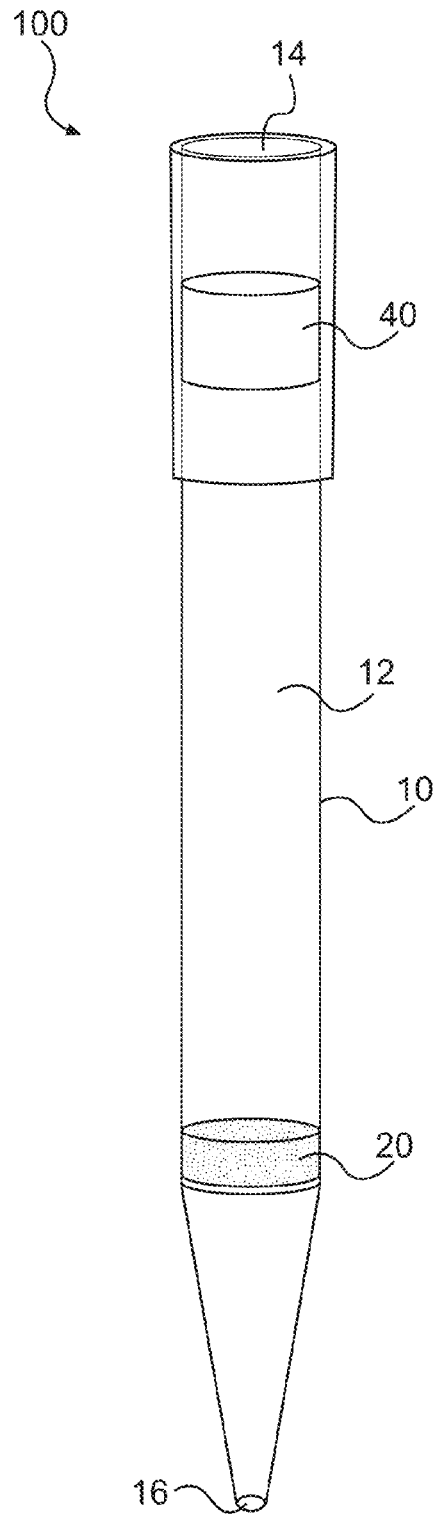

In some embodiments, the pipette tip 100 further contains a pre-filter 30 placed between the second opening 16 and the sample filter 20 (FIG. 1C). The pre-filter 30 has a pore size that is larger than the pore size of the sample filter 20 and does not bind specifically to nucleic acids. In yet another embodiment, the pipette tip 100 contains an aerosol filter 40 in the proximity of the first opening 14 to prevent contamination from the pumping device (FIG. 1D).

Sample Preparation, Binding, Washing and Eluting Conditions

Figure 2A:
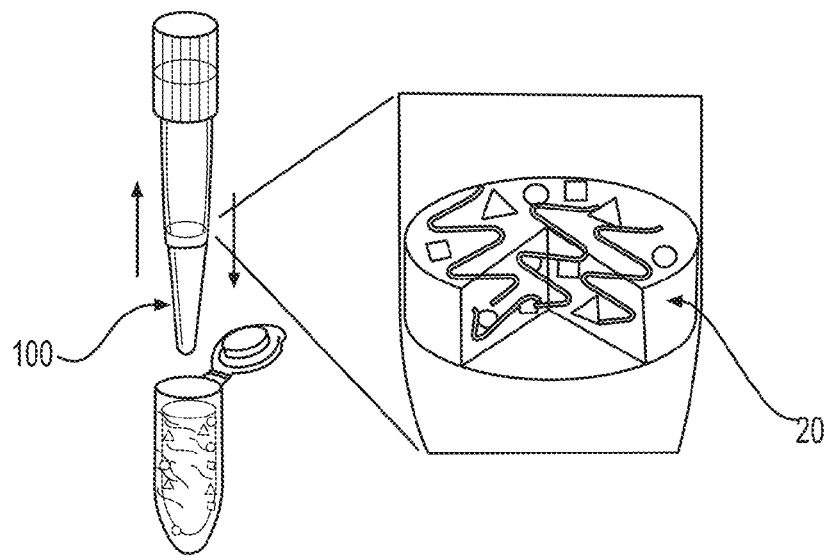
FIGS. 2A-2D are schematic illustrations of an exemplary process for purifying fetal nucleic acids in accordance with the present application.

The sample preparation step typically contains a lysis step to release the nucleic acids of interest from the original host, such as cells, bacteria or virus. The lysis of the cellular or viral structure can be achieved chemically (e.g., NaOH or guanidine thiocyanate), mechanically (e.g., glass beads or sonication), or physically (e.g., freeze-thaw cycles). For tissue samples, an enzyme digestion step may be employed before the lysis step. The lysed sample is then loaded onto a monolithic filter of the present application for isolation of nucleic acids. FIGS. 2A-2D shows a typical process of purifying nucleic acids using the pipette tip 100 of the present application. First, the sample material is passed (or flowed) through the filter 20 toward the pipetting instrument, filtering the contents so that nucleic acids in the sample are retained on the filter 20. Preferably, the sample material is passed back through the filter 20 toward the inlet 16 and then passed back and forth through the filter 20 multiple times (e.g., 2-5 times, 2-10, times, 2-25 times, 2-20 times, 5-10 times, 5-15 times, 5-20 times, 10-15 times, 10-20 times or 15-20 times) to improve binding efficiency. In some cases the sample material is passed back and forth through the filter 20 at least 2 times, 5 times, at least 10 times, at least 15 times, or at least 20 times or more. Typically, fluids are flowed across the filter in a first direction and then flowed across the corresponding filter in a direction opposite the first direction resulting in a flow-through fraction passing through the filter at least twice (FIG. 2A).

Nucleic acids may be bound to the filters using suitable binding buffers. Depending on the target for binding (e.g., HMW DNA, LMW DNA or both), suitable binding conditions can be achieved by adjusting the concentration of one or more chaotropic agents and/or chaotropic salts thereof. Exemplary chaotropic agents include, but are not limited to chaotropic salts, such as urea, thiourea, sodium dodecyl sulfate (SDS), guanidine isothiocyanate, guanidine hydrochloride, sodium chloride, magnesium chloride, sodium iodide, potassium iodide and sodium perchlorate; aliphatic alcohols, such as butanol, ethanol, propanol and isopropanol; phenol and other phenolic compounds; arginine, and magnesium chloride. Exemplary chaotropic salts include guanidinium thiocyanate, guanidinium chloride, sodium iodide, sodium perchlorate, lithium perchlorate, urea and thiourea In some embodiments, binding buffers are utilized to promote binding of both HMW and LMW DNA to a selected filter in a first step, wherein an aliphatic alcohol, such as isopropanol is provided in a range between about 17% to about 25%, preferably between about 20% to about 24% (optimal=22.5%) and a chaotropic salt, such as guanidine isothiocyanate and/or guanidine hydrochloride is provided in a range between about 0.5 M to about 4.0 M, preferably between about 1.0 M to about 2.5 M (optimal=1.8 M). To promote selective binding of HMW DNA to a selected filter, an aliphatic alcohol, such as isopropanol may be provided in a range between about 0% to about 10%, preferably between about 4% to about 6% (optimal=4.7%) and a chaotropic salt, such as guanidine isothiocyanate and/or guanidine hydrochloride is provided in a range between 1.0 M to 4.0 M, preferably between about 3.0 M to about 4.0 M. To promote binding (and concentration) of recovered LMW DNA to a selected filter, an aliphatic alcohol, such as isopropanol may be provided in a range between about 10% to about 25%, preferably between about 15% to about 20% (optimal=17.7%) and a chaotropic salt, such as guanidine isothiocyanate and/or guanidine hydrochloride is provided in a range between about 1.0 M to 5.0 M, preferably between about 2.0 M to about 4 M (optimal=3.3 M).

In the next step (FIG. 2B), the filter 20 is washed with a wash buffer to remove materials that do not specifically binds to the filter. Similar to that in Step 1, the wash buffer is passed back and forth through the filter 20 at least 1 time, 5 times, at least 10 times, at least 15 times, or at least 20 times or more. In some embodiments, the filter 20 is washed with a single wash buffer before the next step. In other embodiments, the filter 20 is washed with two or more wash buffers before the next step. This step is an optional step that may not be needed in some embodiments.

The wash step removes extraneous, unbound materials present in the nucleic acid extracts or fractions. Examples of wash buffers include, but are not limited to, buffers containing guanidine, sodium acetate, and ethanol), buffers containing Tris and ethanol, acetone, ethanol, mixtures of acetone and ethanol, and other solvents that evaporate easily to dry the filter.

In the next step (FIG. 2C), the filter 20 is dried by passing air through the filter 10, 20, 30, 40, 50, 60, 70, 80, 90, 100 or more times. This step removes the excess liquid from the filter 20 and allows elution of the bound nucleic acid in a smaller volume. This step also removes the residual solvents from the binding and/or washing step because such residual solvent may negatively affect subsequent reactions such as PCR. This step is an optional step that may not be needed in some embodiments.

In the next step (FIG. 2D), the nucleic acid bound to the filter 20 is eluded from the filter by a elution buffer. The elution buffer may be passed back and forth through the filter 20 at least 2 times, 5 times, at least 10 times, at least 15 times, or at least 20 times or more.

Nucleic acids may be eluted from the filters using suitable elution buffers. Suitable elution conditions can be achieved by adding an elution buffer, Examples of elution buffers include, but are not limited to, 1 mM NaOH, 10 mM TrisHCl or any low salt buffer or water, preferably pH above 6.5.

In some embodiments, the methods described herein allow for 1) isolation of a range of DNA fragment lengths from large volumes of sample; and 2) selective isolation of DNA fragments in a certain size range.

By embedding a monolithic binding matrix within a pipette tip, the extraction process and instrumentation required to purify nucleic acids from difficult sample types is greatly simplified. The geometry and porosity of the binding matrix is tailored to minimize fluidic impedance or clogging, while providing a large surface area for nucleic acid binding within pipette tips ranging from 0.1 to 50 ml in total volume. The matrix is therefore microfluidic friendly, since low pressures can be used to drive samples through it. Bidirectional flow during sample aspiration and dispensing allows for prolonged residence time between the sample extract and the binding matrix for optimal nucleic acid recovery and elution, and enables relatively large sample volumes to be processed without clogging within a single filter tip. The pipette tip format is universal to any device that pumps liquid, from a hand-held pipette that is useful in environments where sample numbers are low or resources are limited to large liquid handling systems capable of processing many samples simultaneously.

Separation of Low Molecular Weight Nucleic Acids From High Molecular Weight Nucleic Acids In one aspect, the present application provides a method for concentrating and separating low molecular weight (LMW) nucleic acids (e.g., fetal nucleic acids) and/or high molecular weight (HMW) nucleic acids (e.g., maternal nucleic acids) from a sample containing both LMW nucleic acids and HMW nucleic acids using one or more filters that bind specifically to LMW nucleic acids and/or HMW nucleic acids. The method comprises the steps of passing the sample through a first filter that binds both the LMW nucleic acids and the HMW nucleic acids, recovering bound nucleic acids from the first filter, passing the recovered nucleic acids through a second filter under conditions that allow binding of the HMW nucleic acids to the second filter to produce a flow through fraction, wherein the flow through fraction contains the LMW nucleic acids. In some embodiments, the method further comprises the steps of eluting the HMW nucleic acids from the second filter, then passing the flow through fraction containing the LMW nucleic acids through the second filter under conditions that allow binding of the LMW nucleic acids to the second filter, and eluting the LMW nucleic acids from the second filter. Alternatively, the method may further comprises the steps of passing the flow through fraction containing the LMW nucleic acids through a third filter under conditions that allow binding of the LMW nucleic acids to the third filter, and eluting the LMW nucleic acids from the third filter. In some embodiments, the first and the second filters are the same filter. In other embodiments, the first filter and/or the second filter each comprises two subfilters of different porosity. In some embodiments, the subfilters are placed apart from each other. In other embodiments, subfilters are placed adjacent to each other without any space between the subfilters. In yet other embodiments, the subfilters are fused to each other to form a single monolithic structure with two sections of different porosity. In some embodiments, the first and second filter are the same filter with two sections of different porosity.

In some embodiments, the method described above (i.e., separation of DNA based on size exclusion or enrichment) is used in isolation of cell-free DNA from clinical samples, which are usually large in volume. Examples of such clinical samples include, but are not limited to, samples from pregnant females (for separation of maternal and fetal DNA), samples from cancer patient (for separation of normal DNA from tumor DNA), samples from transplant patient (for separation of host from donor DNA). In some other embodiments, the above-described method is used for in the library preparation protocol prior to performing Next Generation Sequencing or for isolation of infectious diseases from renal samples.

In some embodiments, the method is used for separating and isolating fetal nucleic acids from maternal nucleic acids in a plasma sample. In particular, the method utilizes filters with defined pore sizes for the capture and concentration of both HMW nucleic acids (e.g., maternal nucleic acids) and LMW nucleic acids (e.g., fetal nucleic acids). This is followed by the capture (and exclusion) of HMW nucleic acids and retainment and concentration of the LMW fetal nucleic acids.

In preferred embodiments, the filters are placed within pipette tips so that a sample can be loaded onto the filters and eluded from the filters by pipetting the sample through the pipette tips. The pipette tip format is amenable to automation on a variety of liquid handling instruments to provide high-throughput processing capabilities.

In one particular embodiment, the method includes: a) flowing a plasma sample comprising fetal nucleic acids and maternal nucleic acids through the interior volume of a first pipette tip comprising a first monolithic glass frit under conditions that allow both fetal nucleic acids and maternal nucleic acids to bind to the first monolithic glass frit, (b) flowing a first elution buffer through the first monolithic glass frit to elute bound nucleic acids, (c) flowing eluted nucleic acids through a second pipette tip comprising a second monolithic glass frit under conditions that favor binding of the maternal nucleic acids to the second monolithic glass frit and collecting the flow through fraction of the eluted nucleic acids, (d) eluting bound maternal nucleic acids from the second pipette tip, (e) flowing the flow through fraction through the second tip again under conditions that favor binding of the fetal nucleic acids to the second monolithic glass frit, and (f) eluting the fetal nucleic acids to the second monolithic glass frit.

The sample can be any liquid sample containing nucleic acids of different sizes. The method can be optimized to allow separation of nucleic acids in one size range (e.g., 50-600 bp) from nucleic acids in another size range (e.g., longer than 600 bp). In some embodiments, the sample is a body fluid sample, such as blood, plasma, urine, saliva, lymph fluid or spinal fluid. In a particular embodiment, the sample is a plasma sample from a pregnant female.

The term "LMW nucleic acids" and "HMW nucleic acids," when used in the context of fetal DNA extraction from maternal blood or plasma, refer to nucleic acids in two different size groups. Nucleic acids in the "LMW nucleic acids" group have sizes that are smaller than those of nucleic acids in the "HMW nucleic acids" group. In some embodiments, the term "LMW nucleic acid" refers to nucleic acids of 1000 bp or smaller and the term "HMW nucleic acid" refers to nucleic acids that are larger than 1000 bp. In other embodiments, the term "LMW nucleic acid" refers to nucleic acids of 800 bp or smaller and the term "HMW nucleic acid" refers to nucleic acids that are larger than 800 bp. In other embodiments, the term "LMW nucleic acid" refers to nucleic acids of 600 bp or smaller and the term "HMW nucleic acid" refers to nucleic acids that are larger than 600 bp.

In exemplary embodiments, the method is used for isolation of fetal DNA (typically smaller than 600 bp) from maternal DNA (typically larger than 600 bp) in a plasma sample. The first step of the method utilizes a first pipette tip of 1-50 ml that contains a first glass frit filter having a porosity that allows for thicker plasma samples to flow through the matrix without clogging and the thickness allows for optimal binding of the smaller fragments. In some embodiments, the first pipette tip has a tip volume of about 20 ml, about 10 ml, about 5 ml, about 2 ml, about 1 ml, about 0.5 ml or about 0.1 ml. Suitable plasma sample volume is between about 1 to about 20 ml. In some cases, a sample may be distributed among multiple pipette tips (e.g., 2-4) to increase the volume of sample processed. The tip may be used with a motorized pipette filler, the method described herein can be carried out using various devices, including syringe pumps, hand-held syringes, or other type of automated or manual methods for moving liquid across the glass frit or other type of filter. Columns, syringes or other housing for the filter of different volumes and designs can also be employed as long as the dimensions accommodate a large enough filter. In some embodiments, the first glass frit filter has a pore size of 16-40 micron. In other embodiments, the first glass frit filter is a fused filter having a first section with a pore size of 100-160 micron and a second section with a pore size of 16-40 micron. In yet other embodiments, the first glass frit filter is a fused filter having a first section with a pore size of 16-40 micron and a second section with a pore size of 4-5.5 micron or 4-10 micron. The first glass filter may have a thickness of 2-6 mm, preferably 4 mm, and a diameter of 5-10 mm, preferably 7-8 mm. In one embodiment, the tip is attached to a motorized pipette filler with adaptor. This set-up may be used for extraction of fetal nucleic acids from 10-20 ml plasma using the above-described bind, wash, dry and elution steps.

The binding condition for the first glass frit filter is optimized for binding of both fetal DNA and maternal DNA to the filter. In some embodiments, the binding mixture includes plasma, reagents for digestion, solubilization and denaturation of cellular material and other proteins present in plasma, including enzymes such proteinase K, detergents such as Triton, SDS, and Tween, and denaturants such as guanidine, and/or reagents that facilitate binding of the DNA of the desired size range to the filter, such as guanidine, isopropanol and sodium acetate. In some embodiments, the binding mixture contains isopropanol or ethanol at a final concentration of 17-25% v/v, preferably about 22.5% v/v, and guanidine isothiocyanate and/or guanidine hydrochloride at a final concentration of about 0.5-4 M, preferably 1.8M. Such a binding mixture allows both the fetal DNA and the maternal DNA in the binding mixture to bind to the first glass frit filter. After passing the binding mixture through the first glass frit filter in both directions (i.e., passing the filter in one direction to enter the pipette tip and passing the filter in another direct to exit the pipette tip) for one or more rounds for binding of the fetal DNA and maternal DNA to the filter, the bound DNA is eluded from the first filter with an elution buffer. In some embodiment, the first filter is washed one or more times with a wash buffer. Elution of the bound DNA, which contains both the fetal and maternal DNA. In some embodiments, the bound DNA is eluted in a volume of 0.01-5 ml, 0.01-2.5 ml, 0.01-1 ml, 0.01-0.5 ml, 0.01-0.25 ml, 0.01-0.1 ml, 0.01-0.05 ml, 0.05-5 ml, 0.05-2.5 ml, 0.05-1 ml, 0.05-0.5 ml, 0.05-0.25 ml, 0.1-5 ml, 0.1-2.5 ml, 0.1-1 ml, 0.1-0.5 ml, 0.1-0.25 ml, 0.25-5 ml, 0.25-2.5 ml, 0.25-1 ml, 0.25-0.5 ml, 0.5-5 ml, 0.5-2.5 ml, 0.5-1 ml, 1-5 ml, 1-2.5 ml or 2-5 ml. In some embodiments, the bound DNA is elected in a volume of about 0.05 ml to about 1 ml, or about 0.25 ml to about 0.5 ml so as to concentrate the fetal and maternal DNA. In applications where no enrichment of a subpopulation of DNA is required, this step is the last step of the DNA extraction process and the DNA is typically eluted in a volume of 50-100 µl.

The second step of the method involves removal of the maternal DNA from the DNA sample eluted from the first filter. In some embodiments, this step is accomplished with a pipette tip of 0.2-2 ml, preferably 1 ml, that contains a second glass frit filter. In some embodiments, the second glass frit filter has a pore size of 16-40 micron. In other embodiments, the second glass frit filter has a pore size of 4-10 micron. In other embodiments, the second glass frit filter is a fused filter having a first section with a pore size of 100-160 micron and a second section with a pore size of 16-40 micron. In yet other embodiments, the second glass frit filter is a fused filter having a first section with a pore size of 16-40 micron and a second section with a pore size of 4-10 micron. The second glass filter may have a thickness of 2-6 mm, preferably 4 mm, and a diameter of about 2-6 mm, preferably about 4 mm.

The binding mixture in this step is optimized for binding the maternal DNA, but not the fetal DNA, to the second glass frit filter. In some embodiments, the binding mixture contains isopropanol or ethanol at a final concentration of 0-10% v/v, preferably about 4.7% v/v, and guanidine isothiocyanate and/or guanidine hydrochloride at a final concentration of about 1.0-4.0 M, preferably 3.4M. After passing the binding mixture through the second glass frit filter in both directions (i.e., passing the filter in one direction to enter the pipette tip and passing the filter in another direct to exit the pipette tip) for one or more rounds for binding of the maternal DNA to the filter, the binding mixture is collected for the next step. The collected binding mixture, which is now designated as the flow through fraction from the second filter, contains fetal DNA and is depleted of maternal DNA.

The third step of the method involves isolation of the fetal DNA from the flow through fraction from the second filter. In some embodiments, this step is accomplished with the same pipette tip used in the second step. In these embodiments, the pipette tip from the second step is first washed with an elution buffer to remove the maternal DNA bound to the second filter in the second step. The washed, maternal DNA-free second filter is then used to isolate the fetal DNA under conditions that favor the binding of the fetal DNA to the second filter. The bound fetal DNA is then eluded from the second filter with an elution buffer in a volume of 0.01-0.1 ml. In other embodiments, a third pipette tip of 0.2-2 ml, preferably 1 ml, that contains a third glass frit filter is used in the third step. In some embodiments, the third glass frit filter has a pore size of 16-40 micron. In other embodiments, the third glass frit filter has a pore size of 4-5.5 micron or 4-10 micron. In other embodiments, the third glass frit filter is a fused filter having a first section with a pore size of 100-160 micron and a second section with a pore size of 16-40 micron. In yet other embodiments, the third glass frit filter is a fused filter having a first section with a pore size of 16-40 micron and a second section with a pore size of 4-5.5 micron or 4-10 micron. The third glass filter may have a thickness of 2-6 mm, preferably 4 mm, and a diameter of about 2-6 mm, preferably about 4 mm.

In some embodiments, the above-described steps in fetal DNA purification is carried out using a single filter (i.e., a single tip). The binding of fetal and/or maternal DNA is controlled by the composition of the binding buffer (e.g., binding buffer 1 allows binding of both fetal and maternal DNA to the filter, binding buffer 2 allows only the binding of maternal DNA to the filter, and binding buffer 3 allows only the binding of fetal DNA to the filter). In some embodiment, the single filter is a filter with two sections of different porosity.

Kits

Another aspect of the present application provides a kit for separating and isolating fetal nucleic acids from maternal nucleic acids in a plasma sample. The kit may include any combination of the above described elements. In one embodiment, the kit includes: one or more pipette tips having a frustaconical shape and being dimensioned to fit on the end of a pipetting instrument. The one or more pipette tips comprise a tip comprises a filter comprising a rigid, self-supporting substantially monolithic sintered glass structure with a pore size between about 16 microns and about 40 microns. In some embodiments, the kit further comprises at least one binding buffer formulated to provide conditions for binding maternal nucleic acids to a filter, wherein the conditions include greater than 0% and less than about 10% alcohol and guanidine in a range between about 1.0 M to about 4.0 M; and at least one binding buffer formulated to provide conditions for binding fetal nucleic acids to a filter, wherein the conditions include alcohol in a range between about 10-25% and guanidine in a range between about 1.0 M to about 5.0 M. In some embodiments, the kit further comprises at least one elution buffer suitably formulated to elute DNA from the sintered glass structure and at least one wash buffer suitably formulated to remove extraneous matter not binding to the sintered glass structure. In some embodiments, the one or more pipette tips comprise tip having two or more filters placed therein. In one embodiment, the one or more pipette tips comprise a tip having a glass monolith filter with two sections of different porosity. In other embodiments, the one or more pipette tips comprise a tip having two filters of different porosity, wherein an end of one filter is fused to an end of another filter.

Automated Filter Tip Systems

Any mode of performing the method according to the present application can be employed. However, the attributes, adaptability, simplicity and workflow of the filter tip allow for it to be readily adapted, automated, and effective for a number of clinical sample matrices, input sample volumes, and liquid handling systems. Thus, in a preferred embodiment, the mode of operation includes some kind of automation.

In some embodiments, the present application provides an automated method for purifying nucleic acids from a liquid sample using the filter of the present application. The method comprises: (a) providing an automated robotic platform capable of automatically dispensing reagents, withdrawing sample contents, and moving pipette tips and/or sample tubes; (b) loading the robotic platform with a plurality of pipette tips of the present application, each tip comprising a housing defining a passage way between a first opening and a second opening and a filter occupying a section of the passage way, the filter comprising a monolithic filter material that specifically binds nucleic acids; (c) flowing at least a portion of a liquid sample comprising nucleic acids into a pipette tip, wherein the portion of liquid sample is drawn into the housing via the first opening, such that nucleic acids in the portion pass through and bind to the filter material; (d) expelling the portion of liquid sample from the pipette tip via the first opening, wherein the portion of liquid sample passes through the filter a second time while exiting the pipette tip; (e) eluting the nucleic acids from the filter by flowing an elution buffer in through the pipette tip via the first opening and expelling the elution buffer from the pipette tip via the first opening, wherein the elution buffer passes through the filter while entering and exiting the pipette tip; and (f) repeating steps (c)-(e) in each of the plurality of pipette tips.

In a further embodiment, a wash step is included, wherein the filter is washed by flowing a washing buffer in through the pipette tip via the first opening and expelling the washing buffer from the pipette tip via the first opening such that the washing buffer passes through the filter while entering and exiting the pipette tip. Preferably, the wash step is repeated multiple times in each of the plurality of pipette tips.

In a further embodiment, a dry step is included, wherein the filter is dried by passing air through the filter multiple times. In some embodiments, the filter is dried by passing air through the filter 10, 20, 30, 40, 50, 60, 70, 80, 90, 100 or more times.

In some embodiments, the filter material comprises a sintered glass frit having a pore size between about 2 microns and about 220 microns and/or a thickness between about 2 mm and 6 mm. In certain embodiments, the pipette tip comprises two or more filters of different porosity, wherein each of the two or more filters binds specifically to nucleic acids.

In certain embodiments, the liquid sample is a plasma sample comprising maternal nucleic acids and fetal nucleic acids and a portion of the eluted nucleic acids comprising maternal and fetal nucleic acids released from the first filter are flowed through a second pipette tip comprising a second filter comprising a second filter material, wherein the eluted nucleic acids are flowed up and down through a first opening of the second pipette tip, such that the maternal nucleic acids pass through the pipette tip and bind to the second filter material and the fetal nucleic acids pass through the second filter material and the first opening of the second pipette tip from which they are recovered.

The systems, devices, and methods can be fully automated or semi-automated by programmable logic. In one mode of operation the method is performed in multiwell plates (e.g., 24-well, 96-well etc.). Preferably, the mixtures are mixed by use of automated liquid handling as this will reduce the amount of work that needs to be done in order to prepare the mixtures to be investigated. Automated sampling protocols may also be performed by means of robotics using equipment and methods known in the art.

Any suitable machinery or equipment may be used to move the samples through the automated purification system and its various processing steps. For example, the systems employed herein can use a variety of robotics known in the art to automate the movement of samples, reagents, and other system components. Exemplary robotic systems have capabilities to move samples on one, two, or three axes and/or to rotate samples about one, two, or three axes.

Exemplary robotics move on a track which may be situated above, below, or beside the workpieces. Typically a robotic component includes a functional component, e.g., a robotic arm able to grip and/or move a workpiece, insert a pipettor, dispense a reagent, aspirate, etc. A "robotic arm", as used herein, means a device, preferably controlled by a microprocessor, that physically transfers samples, tubes, or plates containing samples from one location to another. Each location can be a unit in the automated purification system. Software for the control of robotic arms is generally available from the manufacturer of the arm.

Robotics may be translated on a track, e.g., on the top, bottom, or side of a work area, and/or may include articulating segments which allow the arm to reach different locations in the work area. Robotics may be driven by motors known in the art, which may be, for example electrically, pneumatically, or hydraulically powered. Any suitable drive control system may be used to control the robotics, such as standard PLC programming or other methods known in the art. Optionally the robotics include position feedback systems that optically or mechanically measure position and/or force, and allow the robot to be guided to a desired location. Optionally robotics also include position assurance mechanisms, such as mechanical stops, optical markers or laser guides, that allow particular positions to be repeatedly obtained.

Exemplary automated sampling protocols may utilize, for example, an Eppendorf epMotion 5070, epMotion 5075, Hamilton STARlet, STAR and STARplus liquid handling robots. Such protocols may be adapted for RNA isolation, genomic DNA isolation from whole blood and fetal DNA extraction and enrichment from maternal plasma as further demonstrated below.

It should be recognized, however, that every clinical sample is unique, and will vary one to the next in viscosity, particulates, mucus, surface contaminants, microbial and/or human genetic backgrounds. Given expected variations in clinical sample composition and intended uses of an automated filter tip sample preparation protocol, it may therefore be necessary to modify certain steps in a filter tip procedure in order to achieve desired results. For example, nucleic acid purity and/or recovery from the filter tips described herein may be affected by a number of parameters, such as (1) sample mixing and homogenization with lysis buffer (and alcohol); (2) flow rates; (3) sample numbers; (4) number and type of wash and (5) drying.

For example, regarding (1), while the filter tips described herein have a relatively large pore size, sample homogenization and liquefaction is very important for efficient cell lysis, and subsequent binding steps to the filter tip matrix. With homogenous and well-liquified lysates, samples can also be passed over the filter tip with higher flow rates, which reduces the overall sample processing time. As demonstrated with the large-volume plasma protocol below, large input sample volumes can be effectively processed with a filter tip, which provides users the opportunity to thoroughly homogenize and liquefy difficult samples (on-line or off-line), with only minor concern over input sample volumes.

Further, it should be appreciated that slower flow rates during nucleic acid binding or elution typically result in higher nucleic acid yields, albeit at the expense of total processing time. Slower flow rates will also minimize the extent of DNA shearing.

The optimum number of aspiration and dispense cycles is dependent upon sample type, total sample volume, and flow rates. Step 1 in FIG. 2A is typically the point at which cycle numbers (and flow rates) may require some empirical optimization, with samples such as nasopharyngeal aspirate representing one of the more challenging lysates to optimize due to the range of NPA viscosities from different patients.

Complete drying of the filter tip matrix is recommended to prevent residual organic solvents from co-eluting with the purified nucleic acid sample and inhibiting downstream processes or tests. Because the filter tip is not dried via centrifugation or vacuum filtration, it is important to maximize both the flow rate and cycle numbers during the drying step. Sometimes there is a residual droplet of wash solution on the terminus of the filter tip after the drying cycles are completed. The Hamilton robot has the ability to perform a "tip touch" on the side of the well to release the droplet, thereby ensuring a solvent-free elution. The epMotion system does not have this feature, but a pre-rinse of the filter tip terminus in elution buffer can be programmed to achieve the same effect.

Because the geometry, pipette tip material, and attachment method to the robotic channel arms are unique for each instrument manufacturer, a different filter tip construct is required for each liquid handling system. The filter tip matrix dimensions (diameter, thickness, and pore size) do correlate with nucleic acid binding capacity (and elution efficiencies), as is expected for any solid-phase extraction technique. While thick (>4 mm) matrices may be embedded into a 1 ml filter tip to increase nucleic acid binding capacity for large-volume samples and/or equalize the matrix binding capacity across specific filter tip formats, there is a tradeoff between filter tip thickness and flow rates during the initial binding step (in the presence of crude lysates). Thus, it is sometimes advantageous to embed larger-diameter matrices into larger-volume pipette tips for the initial steps of an automated protocol, (e.g., the 5 ml Hamilton/Akonni Tru-Tips® for large-volume extractions). Given the specific filter tip configurations dictated by the manufacturers of liquid handling robots, however, it is not reasonable to expect the filter tip nucleic acid yields to be identical across liquid handling platforms from different manufacturers, or across different filter tip sizes. Clinical evaluation of automated filter tip protocols and direct comparisons against commercially available automated systems will be reported in detail elsewhere.

Clinical samples (by definition) will contain significant quantities of human genomic DNA unless they are acquired from normally sterile sites (e.g., cerebral spinal fluid). Sometimes the human genomic DNA is desired, whereas in other applications the human DNA represents an unwanted genomic background. Other times it can serve as a carrier if the desired target nucleic acid is present in trace amounts. The presence of background DNA is usually not problematic as long as the total amount of nucleic acid in the sample does not exceed the binding capacity of the matrix.

In the case of the high-volume plasma extraction protocol described below (FIG. 9), the objective was to isolate (fragmented) fetal DNA in the presence of a 10-20 fold excess of maternal DNA, which is similar to the sample preparation objective of infectious disease tests, except that the sequences are highly congruent and can only be distinguished by highly specific molecular testing and/or size discrimination. In some embodiments, total circulating DNA is isolated using a 5 ml filter tip, and subsequent high-molecular and low-molecular weight fetal DNA are separated through subsequent binding and elution to a 1 ml filter tip by altering the binding buffer conditions. Selective size separation and enrichment of target nucleic acids based on their binding and elution properties to a silica monolith is a significantly different mode of action than achieved by membranes or size exclusion spin columns. Size separation and enrichment of microbial DNA from human genomic DNA may be similarly accomplished via customizing filter tip binding and elution buffers.

Once an automated filter tip protocol is validated, there are relatively few ways to introduce error into the process. Nevertheless, it is possible to set up the liquid handling robots with an incorrect filter tip or by placing reagents in an incorrect reagent trough. In some embodiment, pre-filled, foil-sealed reagent plates are provided to avoid such mistakes. The pre-filled plates can significantly simplify the complexity of an automated procedure, reduce the number of pipette tips and consumables, and minimize the deck space required to perform the extraction. Thereafter, extraction results are typically indicative of the quality of the initial sample, where poor recoveries usually relate to sample degradation (during transport or storage) rather than errors in the extraction method.

The automated protocols further demonstrated herein emphasize the utility of the filter tip matrix itself for processing diverse clinical samples, and how it can be adapted for large volumes and specific liquid handling robots. The simplicity of the filter tip systems of the present application also affords some cost advantages for those interested in purchasing a new, automated nucleic acid purification system, because the primary hardware required for automating filter tip procedures is the pipette channel arm itself rather than magnetic rods, vacuum systems, or on-board centrifuges. Minimizing deck space with filter tip protocols also enables advanced users to integrate upstream or downstream automated processes with the filter tip systems of the present invention. For example Hamilton's easyBlood solution to fractionate whole blood can be incorporated with an automated filter tip extraction method, which would significantly streamline bio-banking processes. Post-extraction processes, such as nucleic acid quantitation and normalization, PCR set-up and DNA sequencing are also readily integrated with filter tips using larger liquid handling platforms.

One aspect of the present application relates to an automated method for purifying nucleic acids from a liquid sample, comprising: (a) loading the robotic platform with a plurality of pipette tips, each tip comprising a housing defining a passage way between a first opening and a second opening and a filter occupying a section of the passage way, wherein the filter specifically binds to nucleic acids and wherein the automated robotic platform is capable of automatically dispensing reagents, withdrawing sample contents, and moving pipette tips and/or sample tubes; (b) flowing at least a portion of a liquid sample comprising nucleic acids in through the first opening of a pipette tip such that the nucleic acids pass through the pipette tip and bind to the filter therein; (c) expelling the portion of liquid sample from the pipette tip via the first opening, wherein the portion of liquid sample passes through the filter a second time while exiting the pipette tip; and (d) eluting the nucleic acids from the filter by flowing an elution buffer in through the first opening of the pipette tip and expelling the elution buffer from the pipette tip via the first opening, wherein the elution buffer passes through the filter while entering and exiting the pipette tip. In some embodiments, the steps (b)-(d) is carried out in each of the plurality of pipette tips.

In some embodiments, the method further comprises the step of washing the filter by flowing a washing buffer in through the pipette tip via the first opening and expelling the washing buffer from the pipette tip via the first opening, wherein the washing buffer passes through the filter while entering and exiting the pipette tip. In a related embodiment, the washing step is repeated two or more times.

In some embodiments, the sample flowing and expelling steps are repeated until all of the liquid sample passes through the filter at least once.

In some embodiments, the filter comprises a self-supporting glass frit. In a related embodiments, the glass frit is a sintered glass frit that has not been treated or coated with an agent that improves binding of nucleic acid. In another related embodiments, the glass frit has a pore size between about 2 microns and about 220 microns and has a thickness between about 2 mm and about 20 mm.

In some embodiments, the liquid sample comprises plasma containing maternal and fetal nucleic acids. In a related embodiment, the pipette tip comprises two or more filters of different porosity, wherein each of the two or more filters binds specifically to nucleic acids.

Another aspect of the present application relates to a method for separating and isolating fetal nucleic acids from maternal nucleic acids in a plasma sample, comprising: (a) flowing a plasma sample comprising fetal nucleic acids and maternal nucleic acids through a first filter under conditions that allow specific binding of the fetal and maternal nucleic acids to the first filter; (b) eluting bound fetal and maternal nucleic acids from the first filter to form a concentrated nucleic acid sample comprising fetal nucleic acids and maternal nucleic acids; (c) flowing the concentrated nucleic acid sample through a second filter under conditions that allow the maternal nucleic acids to bind to the second filter and the fetal nucleic acids to flow through the second filter; and (d) collecting the flow-through fraction from the second filter, wherein the flow-through fraction from the second filter contains fetal nucleic acids.

In some embodiments, the conditions that allow specific binding of the fetal and maternal nucleic acids to the first filter in step (a) comprise forming a first binding mixture that comprises the plasma sample, an aliphatic alcohol in a range between about 17-25% (v/v) and a chaotropic salt in a concentration range between about 0.5 M to about 4.0 M.

In some embodiments, the conditions for binding the maternal nucleic acids to the second glass frit filter in step (c) comprise forming a second binding mixture that comprises the concentrated nucleic acid sample, an aliphatic alcohol in a range between about 0-10% (v/v) and a chaotropic salt in a concentration range between about 1 M to about 4.0 M.

In some embodiments, the method further comprises the steps of: (e1) eluting bound maternal nucleic acids from the second filter to produce a regenerated second filter; (f1) flowing the flow-through fraction from the second filter through the regenerated second filter under conditions that allow binding of fetal nucleic acids to the second filter; and (h1) eluting bound fetal nucleic acids from the second filter in step (f1). In a related embodiment, the conditions for binding the fetal nucleic acids to the second filter in step (f1) comprise forming a third binding mixture that comprises the flow-through fraction from the second glass frit filter, an aliphatic alcohol in a range between about 10-25% (v/v) and a chaotropic salt in a concentration range between about 1 M to about 5.0 M. In some embodiments, the method further comprises the steps of (e2) flowing the flow-through fraction from the second filter through the first filter under conditions that allow binding of fetal nucleic acids to the first filter; and (f20 eluting bound fetal nucleic acids to the first filter in step (e2).

In some embodiments, the first and second filters are self-supporting glass frits. In a related embodiment, the glass frits are sintered glass frits. In another related embodiment, the first glass frit filter has a pore size of 16-40 micron and the second glass frit filter has a pore size of 4-10 micron.

In some embodiments, the method further comprises the steps of: (e3) flowing the flow-through fraction from the second filter through a third filter under conditions that allow binding of the fetal nucleic acids to the third filter; and (f3) eluting bound fetal nucleic acids from the third filter.

In some embodiments, one or both of the first and second filter comprises a glass frit comprising a first section having a first pore size and second section having a second pore size, wherein the first pore size is different from the second pore size.

In some embodiments, the first filter and the second filter are the same filter.

Another aspect of the present application relates to a kit for isolating fetal nucleic acids from maternal nucleic acids in a plasma sample, comprising: a pipette tip comprising a self-supporting glass frit filter, wherein the glass frit filter has a pore size of 2-220 microns and is not treated or coated with an agent that improves binding of nucleic acid to the glass frit filter, a first binding buffer formulated to be mixed with a plasma sample and provide a first binding mixture having about 17-25% v/v of an aliphatic alcohol and a chaotropic salt at a concentration of between about 0.5 M to about 4.0 M; and a second binding buffer formulated to be mixed with a plasma sample and provide a first binding mixture having about 0-10% v/v of an aliphatic alcohol and a chaotropic salt at a concentration of between about 1 M to about 4.0 M.

In some embodiments, the kit comprises a first pipette tip comprising a first glass frit filter and having a tip volume of 0.5-50 ml; and a second pipette tip comprising a second glass frit filter and having a tip volume of 0.5-50 ml. In a related embodiment, the first glass frit filter has a pore size of 16-40 micron and the second glass frit filter has a pore size of 4-10 micron. In some embodiments, the glass frit filter comprises a fused glass frit comprising a first section having a first pore size and second section having a second pore size. In a related embodiment, the first section has a pore size of 100-160 microns and the second section has a pore size of 16-40 microns, or wherein the first section has a pore size of 16-40 microns and the second section has a pore size of 4-10 microns.

EXAMPLES

The following Examples are provided to illustrate certain aspects of the present invention and to aid those of skill in the art in the art in practicing the invention. These Examples are in no way to be considered to limit the scope of the invention in any manner.

Example 1

Automated RNA Extraction from Nasopharyngeal Aspirate

An Eppendorf epMotion 5070 liquid handling robot was used with a large pore Akonni TruTip® matrix embedded in 1.2 ml Eppendorf pipette tips, a 2 ml deep-well plate (USA Scientific), Akonni TruTip® extraction reagents, and nasopharyngeal aspirate as the sample matrix. The epMotion 5070 liquid handling robot only holds up to 8 tips simultaneously, so a baseline automated protocol is described for 8 parallel extractions. However, up to 24 samples can be processed during a single program in one deep-well 96-well sample plate. A separate epMotion program is available (and required) in order to process 16 or 24 samples. The protocol outlined below is for an 8 sample automated script.

Setup:

1.1 Bring nasopharyngeal samples to room temperature before starting the extraction.

Figure 3A:
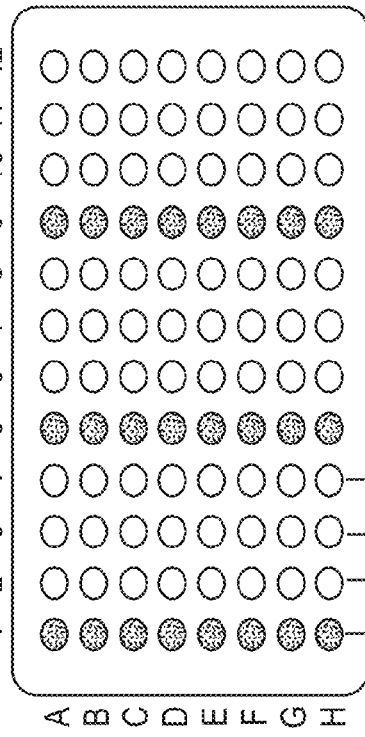
FIGS. 3A-3B depict an Eppendorf epMotion 5070 sample plate layout (A) and arrangement of reagents/consumables on the Worktable (B). The sample plate can be configured for up to 24 samples (columns 1, 5 and 9, respectively), although the epMotion will only process 8 samples simultaneously.

1.2. Aliquot 100 µL nasopharyngeal aspirate plus 150 µL nuclease-free water into column 1 of the sample plate; FIG. 3A).

Figure 2B:
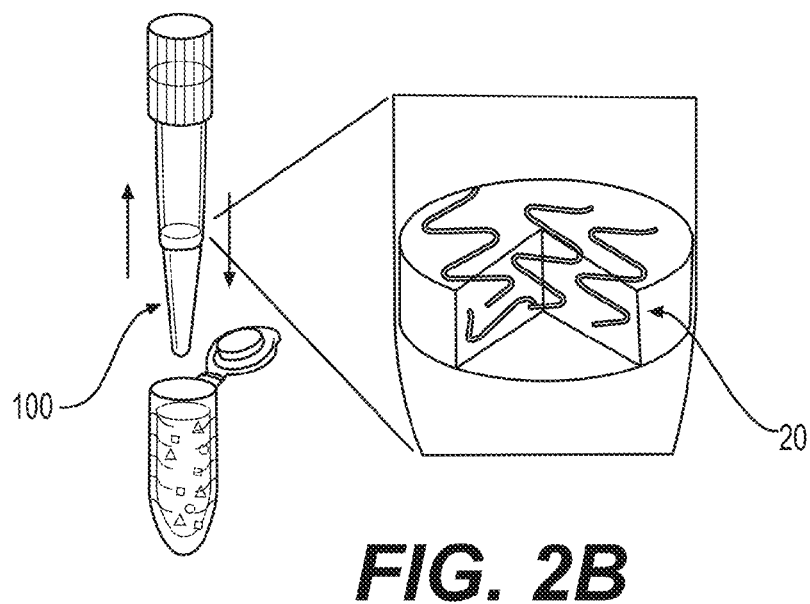
Figure 2C:
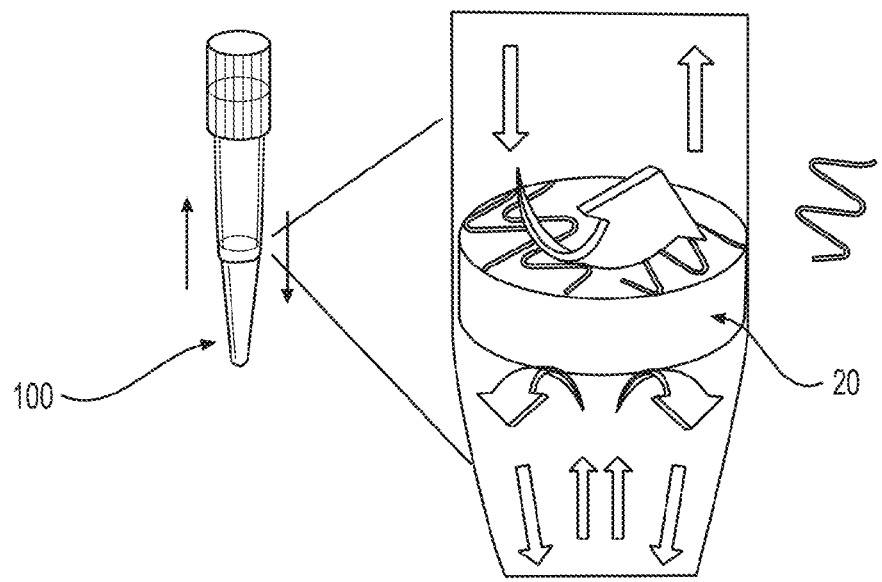
Figure 2D:
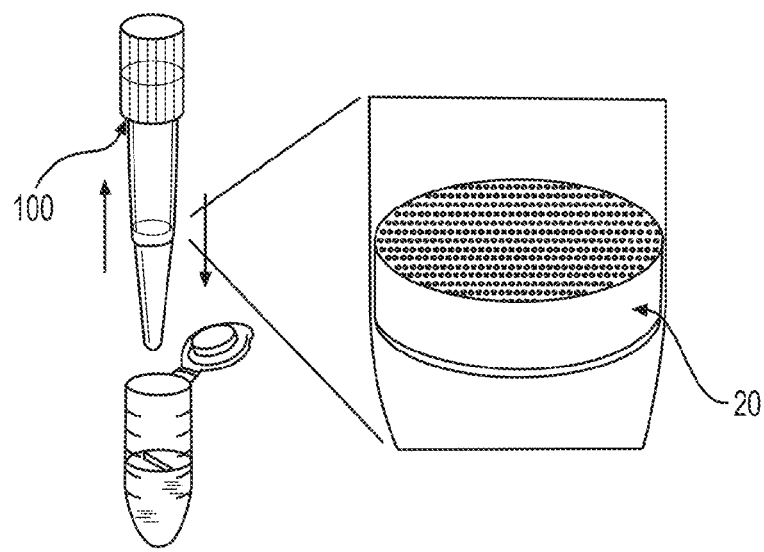

1.3 Place the sample plate into position B1 on the epMotion Worktable (FIG. 2B).

Figure 3B:
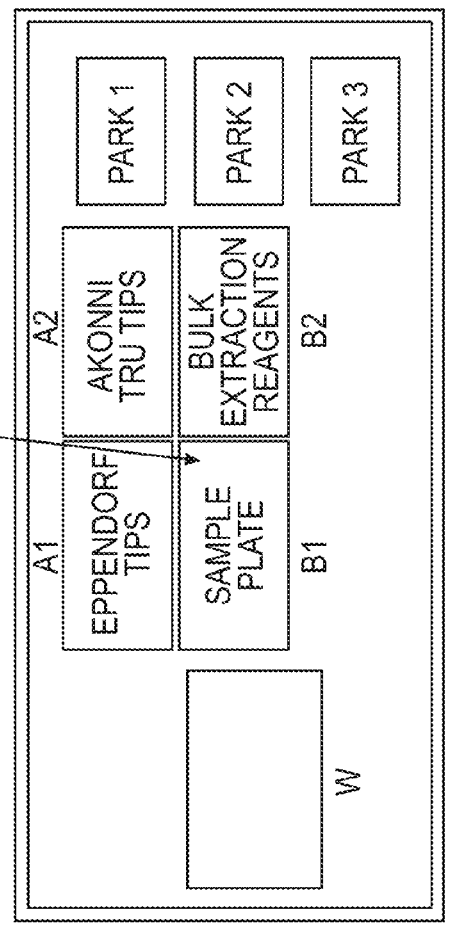

1.4 Place pipette tips, filter tips and 30 nil reagent troughs onto their respective epMotion Worktable positions (FIG. 3B).

1.5 Open the Eppendorf epBlue software, select the Run file provided by Akonni for 8 samples, and load the method by clicking the RUN button on the RUN tab.

1.6 Under Level Sensor Settings, select Levels and Tips, and click the RUN button.

1.7 Input the sample volume into the software and click RUN.

1.8 The epMotion script will prompt the user to add extraction and elution reagents to the reagent reservoirs located at position B2 on the Worktable. Add the recommended volumes of each reagent to the respective trough. For 8 samples, the minimum reagent volumes are depicted in Table 1:

TABLE 1

| Reagent | Volume (ml) | Trough Position |
|---|---|---|
| 95% ethanol | 3.5 | 2 |
| Wash Buffer D | 9.0 | 3 |
| Wash Buffer E | 9.0 | 4 |
| Elution Buffer A2 | 1.3 | 5 |
| Lysis and Binding Buffer D | 11.0 | 6 |

1.9 Input the reagent volumes into the Table presented by the epMotion software during the prompt from Step 1.8 above. The volume of buffer dispensed by the user into each respective reagent reservoir must be greater than or equal to the minimum volumes noted above. If the actual buffer volume is significantly greater than the recommended volumes from Step 1.8, input the approximate volume within each reservoir into the epMotion software Table. Incorrect volume entries could result in incorrect aliquot volumes delivered by the epMotion hardware to each tube or well in the 96-well plate(s).

Automated Program:

1.10 Select RUN to start the automated method. The automated script will move through the following steps (i.e., 1.11-1.23) without user intervention:

Sample Lysis and Reagent Aliquotting:

1.11 Dispense 375 µL Lysis Buffer D into column 1 and mix for 10 cycles (aspirate+dispense=1 cycle). This step starts the lysis incubation process while the remaining reagents are aliquotted.

1.12 Dispense 1.6 ml Wash Buffer D into column 2.

1.13 Dispense 1.6 ml Wash Buffer E into column 3.

1.14 Dispense 50 µL Elution Buffer A into column 4.

1.15 Pause for 6 minutes to complete the 10 minute sample incubation in Lysis Buffer D.

1.16 Add 375 µL ethanol to each well in column 1, mixing each sample with ethanol through 10 pipetting cycles.

Extraction:

1.17 Load 8 filter tips from position A2 on the Worktable, and begin the extraction process outlined in FIGS. 3A and 3B.

1.18 Aspirate and dispense sample/lysis buffer/ethanol mixture from column 1 the Sample Plate for seven cycles to bind the nucleic acid to the TruTip® matrix. Although sample flow through the TruTip® matrix may vary (due to differences in clinical sample viscosity), nucleic acid yield will not be affected. Options for improving sample flow are described in the Discussion.

1.19 Move filter tips to Sample Plate column 2, and cycle Wash Buffer D 5 times over the matrix to remove residual lysis buffer and sample matrix.

1.20 Move filter tips to Sample Plate column 3, and cycle Wash Buffer E 5 times over the matrix to remove proteins and other contaminants from the bound nucleic acid.

1.21 Move filter tips to the empty reagent reservoir position 1 (in Worktable location B2) and cycle 80 times (at a fast flow rate) to dry it the matrix. It is important to thoroughly dry the filter tip, as residual solvents in eluted nucleic acid preparations will negatively affect enzymes such as reverse transcriptase and Taq polymerase.

1.22 Move filter tips to Sample Plate column 4 and cycle 5 times in Elution Buffer A. The extracted and purified nucleic acid is now in elution buffer in Sample Plate column 4 wells.

1.23 Eject filter tips into the epMotion waste bin.

When the program is finished, manually remove the Sample Plate from the instrument and transfer the purified nucleic acid to new tubes for long-term storage or further use. Advanced epMotion users can add instructions to the Run file to transfer eluted samples into separate storage tubes or PCR plates, if desired. The program for 16 total samples will repeat steps 1.11 through 1.16 using Sample Plate columns 5-8. For the 24-sample program, steps 1.11 through 1.16 are repeated 2 more times using Sample Plate columns 5-8 and 9-12, respectively.

Table 2 provides a listing of the reagents and equipment used in Example 1:

TABLE 2

Reagents and equipment used in Example 1.

| | Company | Catalog Number |
|---|---|---|
| Reagent/Material | | |
| TruTip Influenza Extraction Kit (EPM TruTips) | Akonni Biosystems | 300-11120 |
| 95% Ethanol | Acros Organics/Fisher Scientific | AC615110040 |
| 99% Acetone | Sigma-Aldrich | 270725-4L |
| DEPC-treated water | Life Technologies | AM9906 |
| Reagent Reservoir, 30 ml | Eppendorf | 960050100 |
| Deep well plate 96/2000 µL | USA Scientific | 30502302 |
| epT.I.P.S. Motion Filtertips, 1000 µL | Eppendorf | 960050100 |
| Equipment | | |
| epMotion 5070 System | Eppendorf | |
| Dispensing tool TM1000-8 | Eppendorf | 960001061 |
| Reservoir rack | Eppendorf | 960002148 |

Figure 4:
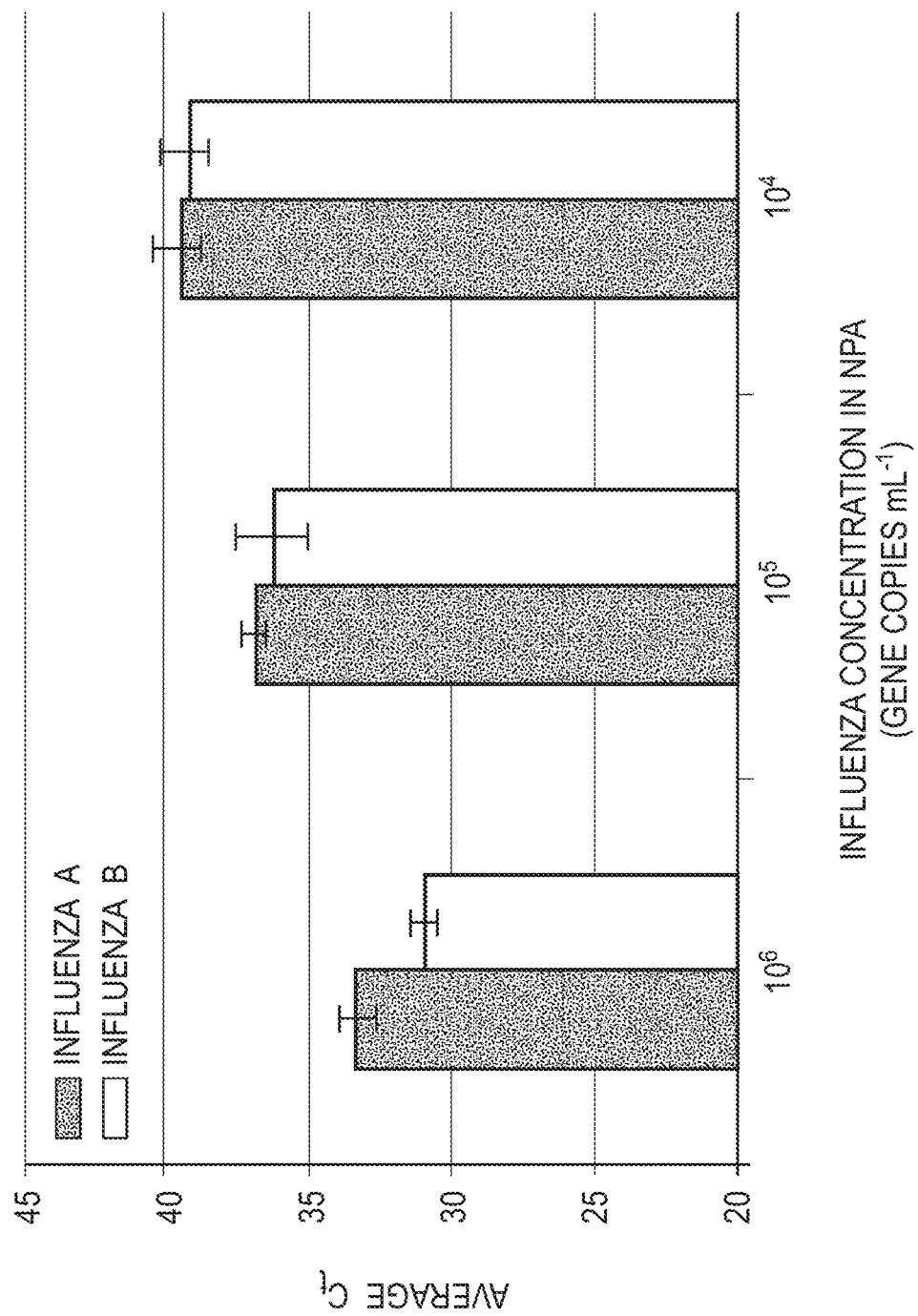
FIG. 4 depicts real-time PCR results from automated extraction of influenza virus admixed in a nasopharyngeal aspirate (NPA). Input NPA volume=100 uL, elution volume=50 uL. Results are the average of 3 replicate extractions from 5 distinct NPA backgrounds (n=15) per dilution level and influenza target. qPCR was performed on the LightCycler 480 system.

Representative Results:

Real-time PCR data for influenza RNA extraction from nasopharyngeal aspirates are shown in FIG. 4. A linear response in average $C_t$ values is observed between $10^4$ and $10^6$ gene copies $ml^{-1}$ of influenza ($R^2$=0.99 and 0.98 for influenza A and B, respectively), with standard deviations in average $C_t$ values less than 1 cycle. The total sample processing time is 16, 28 and 40 minutes for 8, 16 and 24 samples, respectively. Because a typical nasopharyngeal aspirate or swab will contain >$10^4$ $TCID_{50}$ $ml^{-1}$ influenza A or B, representing >$10^7$ gene copies $ml^{-1}$ (assuming 1000 virions per $TCID_{50}$), the automated epMotion protocol is therefore expected to be effective on a majority of clinical NPA specimens.

Example 2

Automatic Extraction of Genomic DNA

A Hamilton STAR liquid handling robot was used to demonstrate automated extraction of 96 samples simultaneously from whole blood. The Hamilton STAR differs from the epMotion system in that an optional heater/shaker unit is available on the deck, which is important for enzymatic digestion of certain clinical matrices, such as whole blood. Because the system can be fitted with a 96-channel pipette head, there is a dedicated 96-well plate for each of the filter tip steps and reagents.

Setup:

2.1 Turn on the STAR instrument and computer.

2.2 Open the Hamilton Run Control software.

2.3 Open the Run file provided by Akonni for 96 samples.

Figure 5:
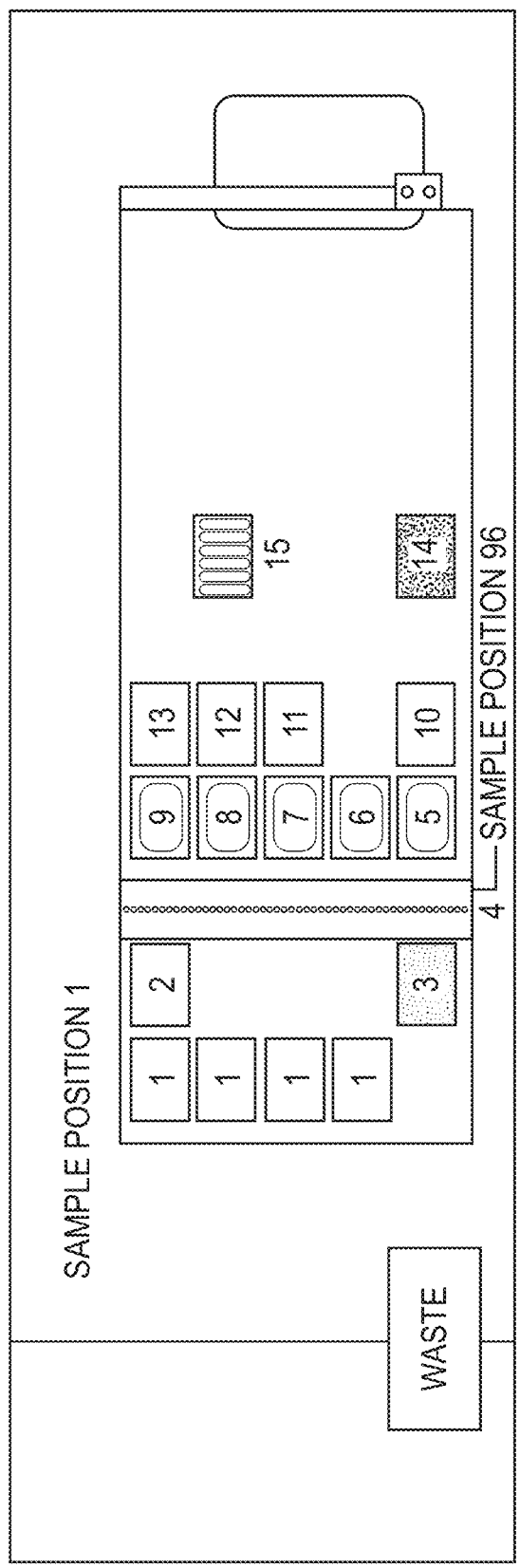
FIG. 5 depicts a Hamilton STAR deck layout for purifying genomic DNA from whole blood (not to scale). Deck Position 1=Hamilton 1 ml filtered tips; 2=Hamilton 1 ml non-filtered tips; 3=Akonni/Hamilton 1 ml LPT 2 mm filter tips; 4=input blood sample carriers (blood collection tubes or microcentrifuge tubes); 5-9=290 ml reagent troughs for Lysis Buffer F, Ethanol, Wash Buffer J, Wash Buffer K and Elution Buffer A2, respectively; 10=96 deep well Binding plate; 11=96 deep well Wash J; 12=96 deep well Wash K; 13=96 deep well Elution plate; 14=Hamilton HHS2 heater/shaker with Nunc 96 deep well Incubation plate; 15=50 ml reagent trough containing proteinase K.

2.4 Place labware onto the STAR deck as shown in FIG. 5.

2.5 Dispense reagents into their corresponding troughs (volumes denote the minimum required to process 96 samples) in accordance with Table 3:

TABLE 3

| Reagent | Volume (ml) | Trough Position |
|---|---|---|
| Lysis and Binding Buffer F | 75 | 5 |
| 95% ethanol | 100 | 6 |
| Wash Buffer J | 175 | 7 |
| Wash Buffer K | 175 | 8 |
| Elution Buffer A2 | 12 | 9 |
| Proteinase K (20 mg $ml^{-1}$) | 8 | 15 |

2.6 Allow samples to equilibrate to room temperature.

2.7 Place the sample tubes in the Sample Carrier racks (deck position 4 in FIG. 5). Place Sample 1 in the rear of the far left carrier and move sequentially down each carrier with Sample 96 ending in the front right position.

Automated Program:

2.8 Select the PLAY button in the upper left of the Run file window. The automated script will move through the following steps without user intervention:Ppp Pre-Treatment:

2.9 Transfer 200 µL from each sample tube to the incubation plate at position 14 on the heater/shaker module (FIG. 5).

2.10 Dispense 80 µL proteinase K into each sample well of the incubation plate.

2.11 Dispense 600 µL Lysis Buffer F into each well of the incubation plate.

2.12 Mix the solution for 10 cycles through the filter tip, and then incubate for 20 minutes at 70° C. and 500 rpm. While the samples are incubating, the liquid handling system continues operating by dispensing reagents into their corresponding plates and wells:

800 µL ethanol into each well of the deep well plate at position 10.

1.6 ml Wash Buffer J into each well of the deep well plate at position 11.

1.6 ml Wash Buffer K into each well of the deep well plate at position 12.

100 μL Elution Buffer A into each well of the deep well plate at position 13.

2.13 After the 20 minute incubation, the sample mixture is transferred from the incubation plate to the deep well plate at position 10, and mixed through 12 pipetting cycles.

2.14 Eject reagent tips into the waste bin.

Extraction

This portion of the gDNA blood procedure is very similar to the epMotion influenza protocol, except for the composition of wash reagents and cycle numbers. The Hamilton TruTips® tips are carbon impregnated to allow for liquid level sensing, so the flow of liquids through the TruTip is not readily visible to the user.

2.15 Load 96 TruTips® from deck position 3.

2.16 Aspirate and dispense the sample/lysis buffer/ethanol mixture in position 10 for 10 cycles to bind nucleic acids to the TruTips® matrix.

2.17 Move the filter tips to position 11 and cycle Wash Buffer J 5 times over the matrix to remove residual lysis buffer and sample matrix.

2.18 Move the filter tips to position 12 and cycle Wash Buffer K 5 times to remove proteins and other contaminants from the bound nucleic acid.

2.19 Cycle the filter tip 40 times at high speed to air dry.

2.20 Move the filter tips to position 13 and cycle 5 times in Elution Buffer A2. The extracted and purified nucleic acid is now in elution buffer in the deep well plate.

2.21 Eject filter tips into the waste bin.

When the program is finished, remove the Elution Plate from the instrument and transfer the extracted samples to the appropriate tubes for storage or downstream applications.

Figure 6A:
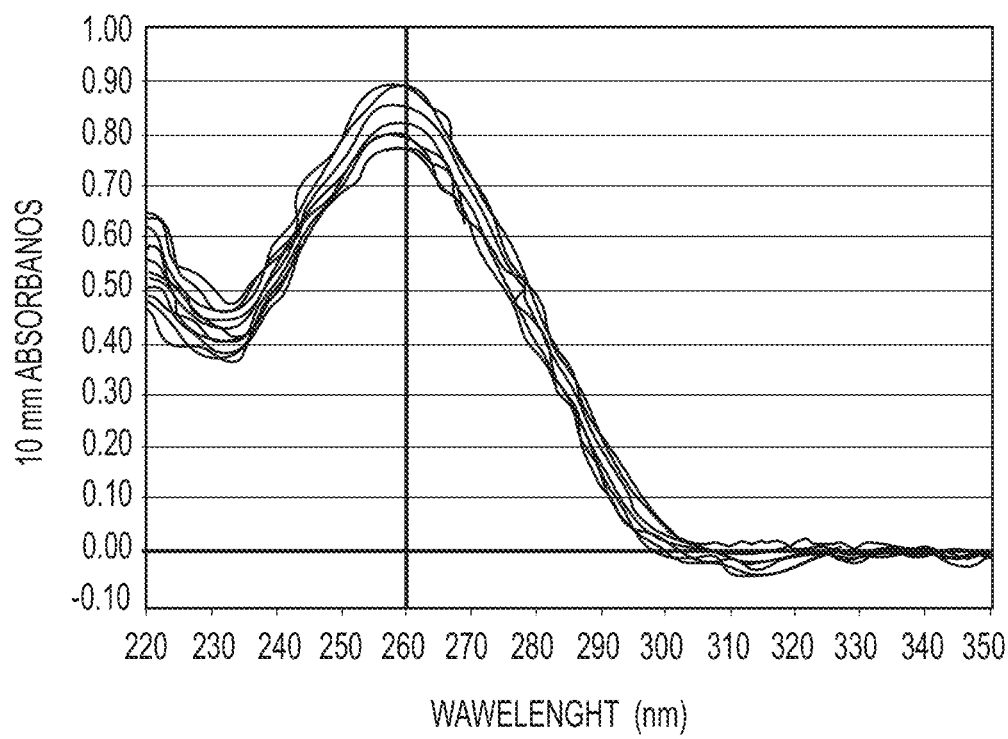
FIGS. 6A-6G shows the results of various genomic DNA (gDNA) extractions.
Figure 6B:
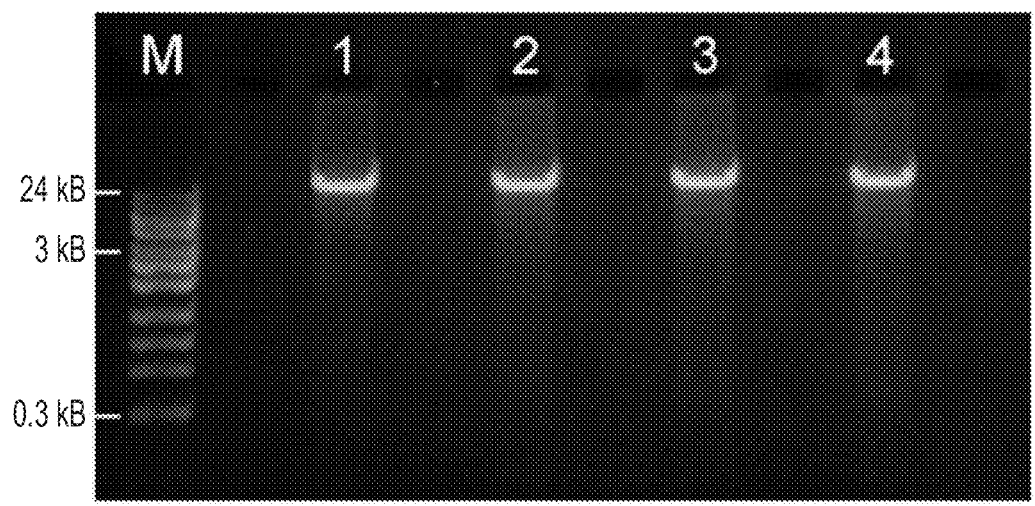

Table 4 provides a listing of the reagents and equipment used in Example 2:

Representative Results:

Given the range of molecular tests performed on human genomic DNA, the primary objective of nucleic acid extraction from whole blood is to produce pure, high molecular weight genomic DNA. The automated protocol for 96 samples is completed within 1 hr. FIG. 6A shows the UV/Vis absorbance profiles for 45 positive blood samples processed simultaneously with 45 reagent blanks on the Hamilton STAR protocol, with an average $A_{260/280}$ ratio of 1.96 and average $A_{260/230}$ ratio of 1.93. An $A_{260/280}$ ratio between 1.7-2.0 and $A_{260/230}$ ratio>1.7 are generally indicative of very pure DNA, free of residual salts, proteins or solvents, and acceptable for most downstream molecular applications. The 1% agarose gel in FIG. 6B shows that the resulting gDNA is of high molecular weight (>24 Kb), with minimal shearing. Human DNA from the full set of 45 positive samples was quantified with the Quantifiler® Human DNA Quantification Kit (Life Technologies) on the LightCycler® 480 system, resulting in an average yield of 5.26±0.46 ug human DNA per 200 uL whole blood.

Table 5 shows the average $A_{260/280}$ ratios from automatically purified gDNA from whole blood, buffy coat, saliva, buccal swab, rat lung, rat liver, rat spleen and rat kidney.

TABLE 5

Genomic DNA quality from various sample types.

| Sample Type | Avg A260/A280 |
| --- | --- |
| Whole Blood | 1.92 |
| Buffy Coat | 1.88 |
| Oragene Saliva | 1.78 |
| Buccal Swab | 1.90 |
| Rat Lung | 1.86 |
| Rat Liver | 2.06 |
| Rat Spleen | 2.10 |
| Rat Kidney | 2.12 |

TABLE 4

Reagents and equipment used in Example 2.

| | Company | Catalog Number |
| --- | --- | --- |
| Reagent/Material | | |
| TruTip gDNA Blood Extraction Kit (Hamilton TruTips ®) | Akonni Biosystems | 300-20341 |
| 95% ethanol | Acros Organics/Fisher Scientific | AC615110040 |
| Proteinase K | Amresco | E195 |
| 1 ml Hamilton filtered CO-RE 96 tip rack | Hamilton | 235905 |
| 1 ml Hamilton non-filtered CO-RE 96 tip rack | Hamilton | 235904 |
| 50 ml Reagent Trough | Hamilton | 187297 |
| Deep Well 2 ml plate | USA Scientific | 1896-2800 |
| Nunc 96 DWP-2 ml | Thermofisher | 27874 |
| Reagent Trough | Fisher | 14-222-412 |
| Equipment | | |
| Hamilton STAR System | Hamilton | |
| 8-channel liquid handling arm | Hamilton | 173027 |
| 96-channel head | Hamilton | 199090 |
| Tip Carriers (TIP_CAR_480BC) | Hamilton | 182085 |
| Sample Carriers (SMP_CAR_32_EPIL) | Hamilton | 173400 for carriers |
| | Hamilton | 182238 for inserts |
| Plate Carriers (PLT_CAR_L5AC) | Hamilton | 182090 |
| Multiflex Carrier | Hamilton | 188039 |
| HHS2 Unit | Hamilton | 199033 |
| Rack Carrier (rackformfx_car_L5_rgt5) | Hamilton | 188047 |

Figure 6C:
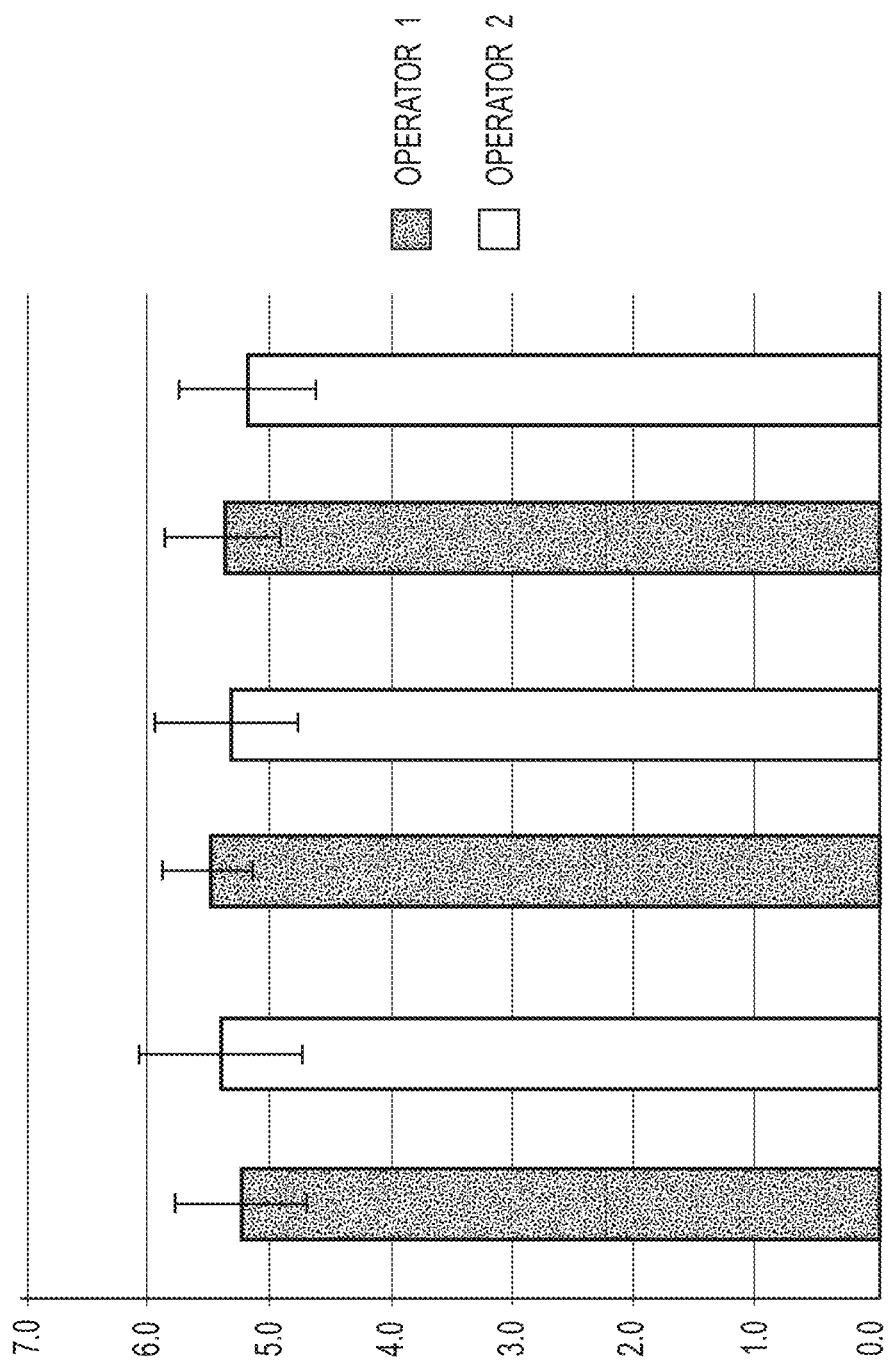
Figure 6D:
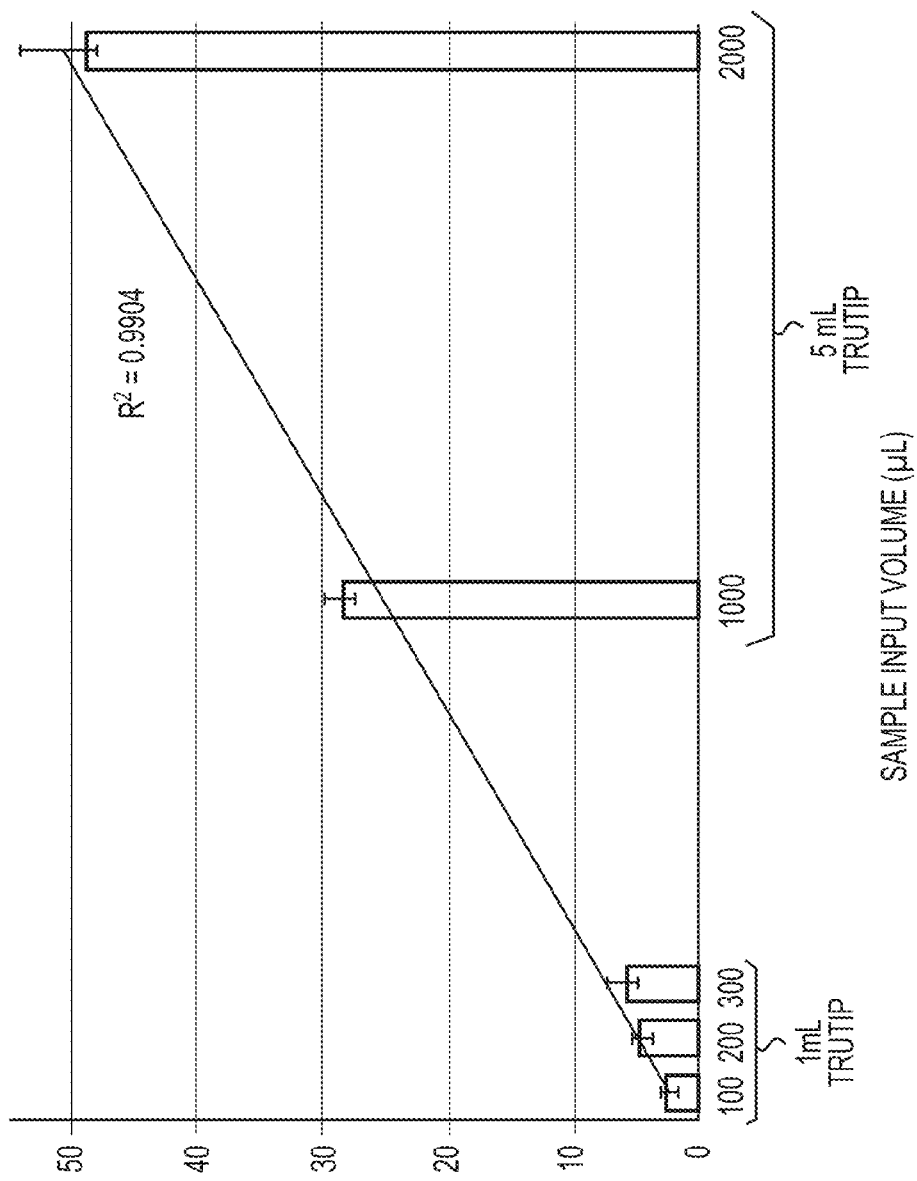
Figure 6E:
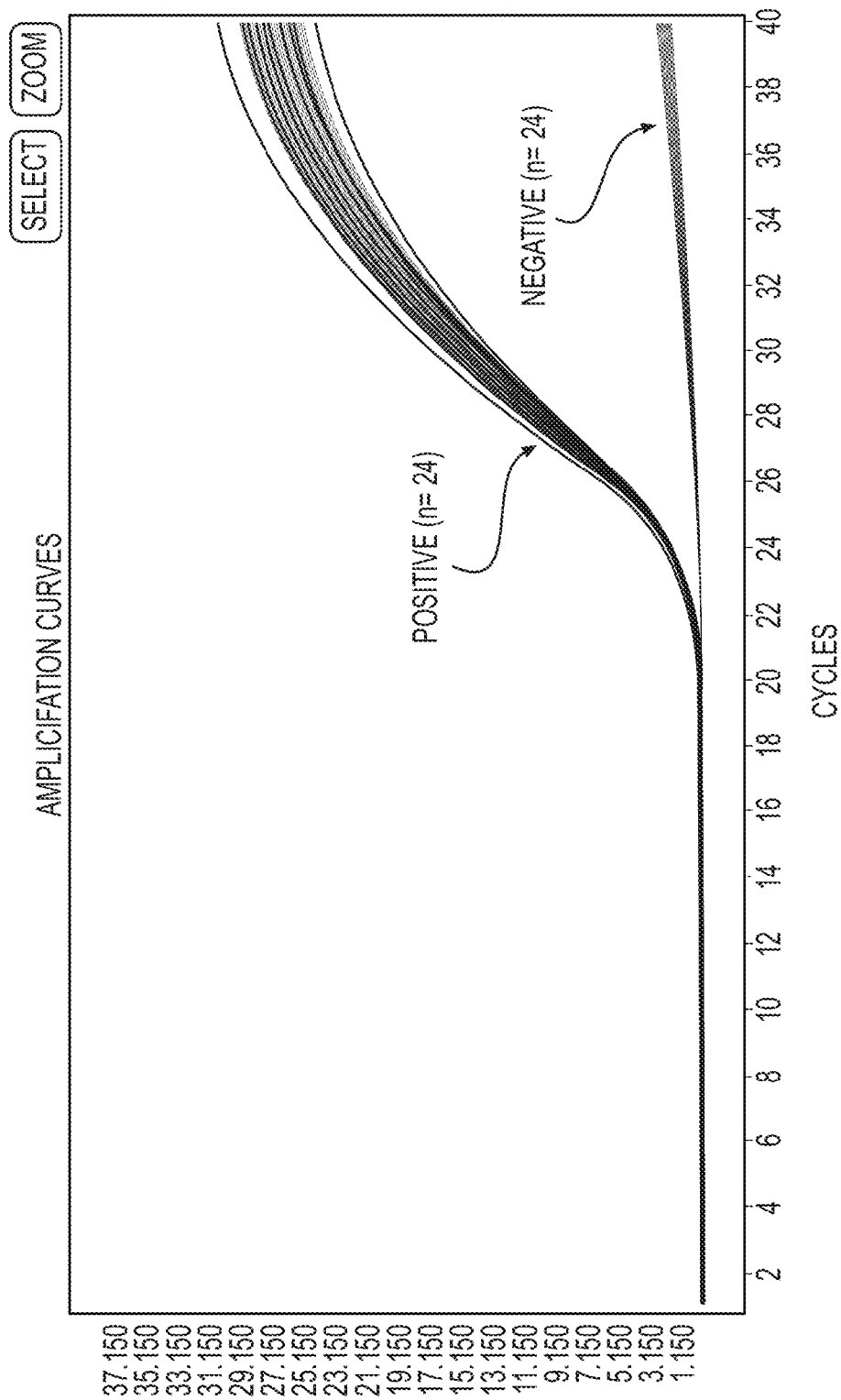
Figure 6F:
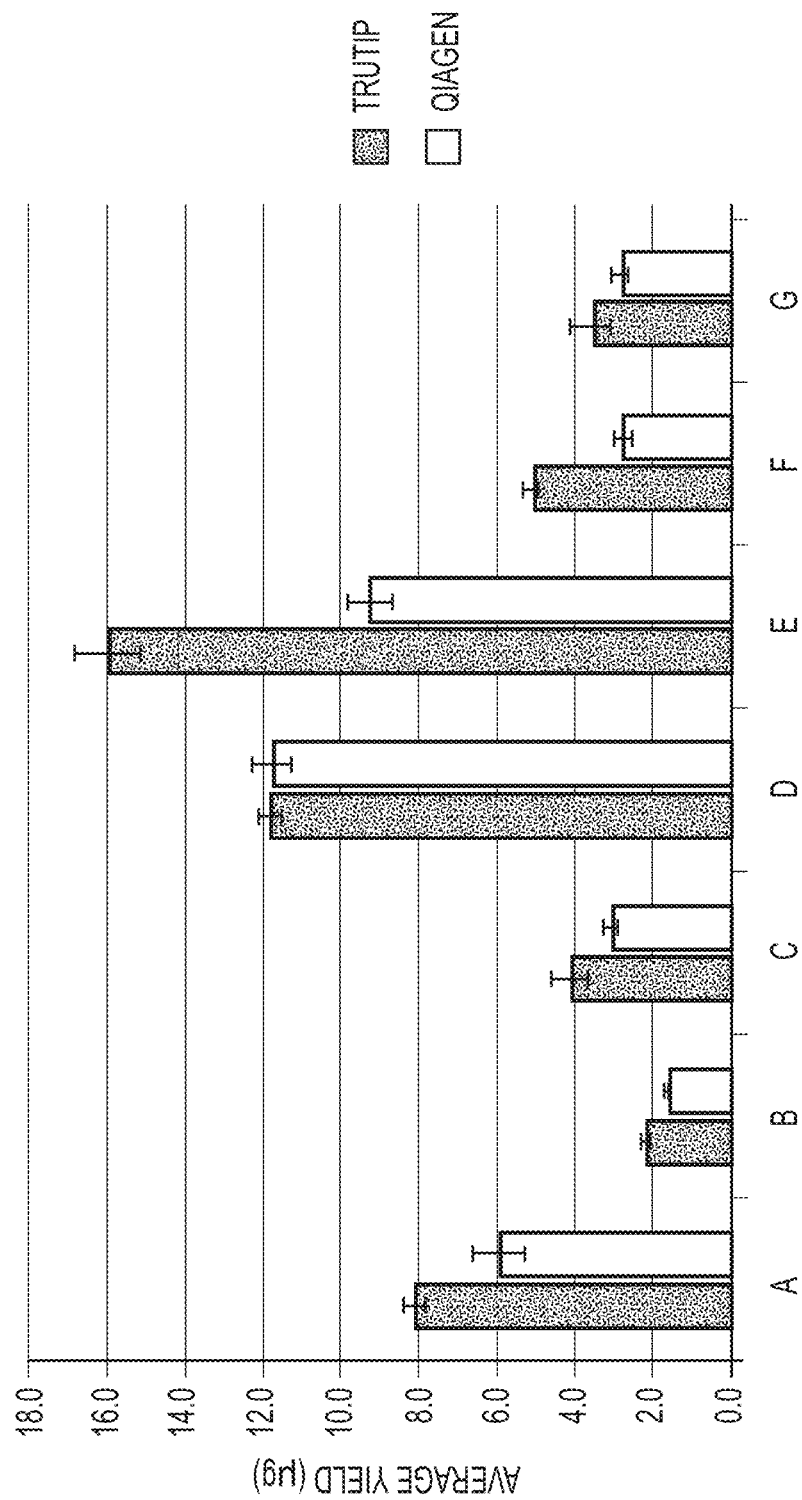
Figure 6G:
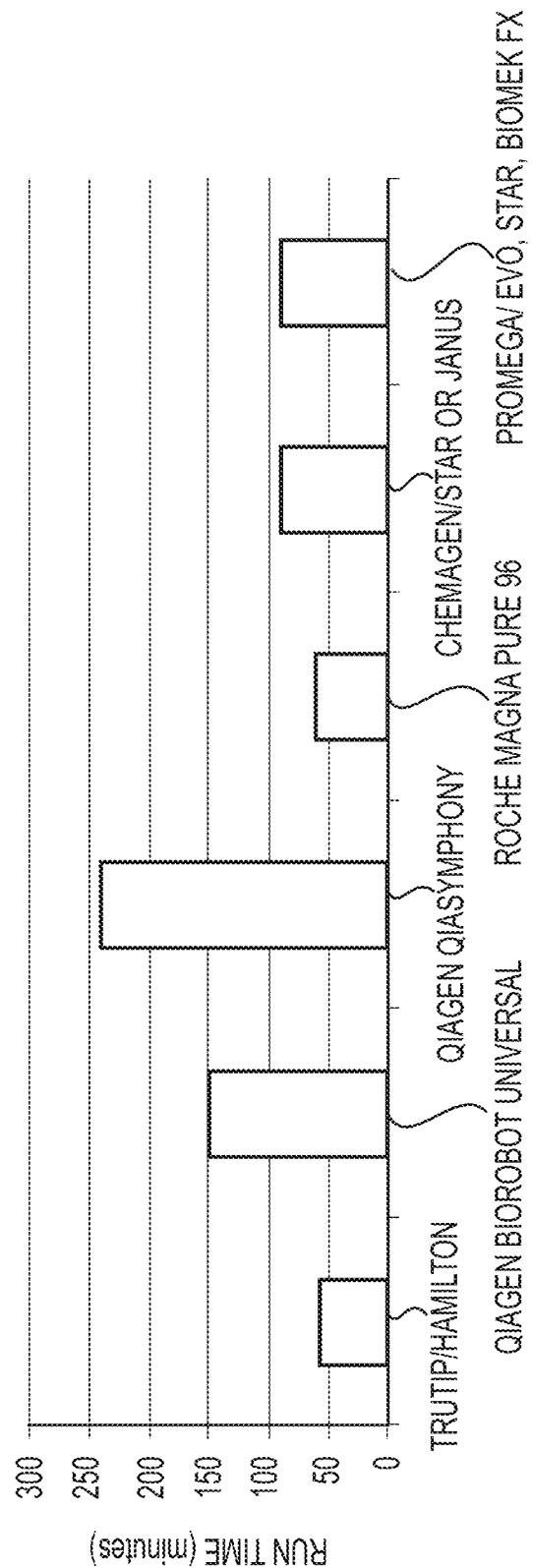

FIG. 6C shows real-time qPCR results from 8 runs each in which 200 µl pooled, whole blood input was processed with a 1 ml TruTip® filter and eluted in a volume of 100 µl. The results shows that the average yield of human DNA isolated by different operators over 3 separate days was highly reproducible. FIG. 6D shows that the average gDNA yields from whole blood was linear over a range of whole blood input volumes of 100 µL, 200 µL and 300 µL processed (8 runs each) from 1 ml TruTip® filters (left side) and whole blood volumes of 1000 µL and 2000 µL processed from 5 ml TruTip® filters (center and right). FIG. 6E shows the results a cross-contamination study in which a plate containing 24 saliva wells and 24 PBS wells was subjected to the automatic DNA extraction process. The extracted DNA from each well was then amplified with qPCR. As shown in FIG. 6E, there was no cross-contamination between wells. FIG. 6F shows UV absorbance results from a comparison of average gDNA yields from 7 individual, blinded saliva samples (Samples A-G; 400 µL input/100 µl elution) extracted using Qiagen's manual spin column method (right column/pairs) and an automated extraction method according to the present invention (left column/pairs). The data suggests that the automatic process of the present application provides a better recovery of sample gDNA than the Qiagen process. FIG. 6G shows the processing times for 200 µl whole blood processed from a TruTip® filter (Column 1) as compared to five other competitor extraction systems (Columns 2-6).

Example 3

Protocol for Purifying Fetal Nucleic Acids

Non-invasive prenatal diagnostics (NIPD) is an important and rapidly growing market offering ground-breaking medical advancements due to its ability to replace the standard prenatal diagnostic methods which carry many risks, including fetal deformation and miscarriage. Instead, testing for genetic abnormalities in fetal DNA present in the mother's plasma only requires a simple blood draw. Though this method offers a lower risk approach to prenatal diagnostics, there are also many challenges with the sample type that require special processing techniques. First, fetal DNA is present at low concentration in maternal plasma early on in the pregnancy, so it is important to be able to process large sample volumes and concentrate them to achieve adequate amounts for analysis. However, current kits available on the market allow input volumes of only 250 µL-5 ml and isolate total nucleic acid. Second, fetal circulating DNA is present in maternal plasma in a high background of maternal circulating DNA (Lo 1997). If the blood sample is not processed in a timely manner (<24 hrs), then the background of maternal DNA increases over time causing a further decrease in the % fetal DNA present (Barrett 2011). This low ratio makes it difficult to accurately quantitate different copy numbers of genes specific to the fetal DNA. Furthermore, the maternal plasma samples, depending on how quickly they are processed, can contain clotting factors and other proteins and coagulants that cause clogging of spin column binding materials. Third, the current kits use silica spin column methods that are not easily automated which is an important capability when moving to a clinical diagnostic assay with regulatory approval.

An exemplary protocol for separating and isolating fetal nucleic acids from maternal nucleic acids in a plasma sample in accordance with the present invention is provided below.

3.1.0 Set-Up
3.1.1 Aliquot 615 µl Proteinase K to each 5 ml Sample Tube (two 5 ml sample tube per sample).
3.1.2 Add 1 µg Carrier RNA (50 µL of 0.2 µg/µl) to each Sample Tube.
3.1.3 Add 6.2 ml Lysis Buffer CN-L1 to each Sample Tube.
3.1.4 Add 5 ml plasma sample to each Sample Tube.
3.1.5 Vortex the Sample Tubes for 30 seconds at maximum speed.
3.1.6 Incubate at 60° C. for 30 minutes in a water bath.
3.1.7 Add 12 ml Binding Buffer CN-B1 to each Sample Tube.
3.1.8 Add 10 µl BSA (20 mg/ml) to each Sample Tube.
3.1.9 Vortex the Sample Tubes for 15 seconds at maximum speed.
3.1.10 Incubate Sample Tubes on ice for 5 minutes
3.2.0 Extraction:
3.2.1 Binding of fetal and maternal DNA to Filter
3.2.1.1 Attach a 20 ml Pipette Tip to a motorized pipette filler.
3.2.1.2 Pipette liquid in Sample Tube A for 18 cycles (cycle=aspirate+dispense).
3.2.1.3 Repeat Step 3.2.1.2 for Sample Tube B.
3.2.1.4 Discard sample tubes (containing liquid sample) but retain the Pipette Tip.
The nucleic acid is now bound to the Pipette Tip Filter.
3.2.2 Wash
3.2.2.1 Using motorized pipette filler, pipette wash buffer through Pipette Tip for 1 cycle.
3.2.2.2 Discard wash buffer but retain the Pipette Tip.
3.2.2.3 Repeat step 3.2.2 three more times.
The nucleic acid is still bound to the Pipette Tip Filter.
3.2.3 Dry
3.2.3.1 Using motorized pipette filler, pass air through the Pipette Tip Filter for 15 cycles. Gently tap the Pipette Tip intermittently if a noticeable amount of Wash Buffer is left.
This step is to avoid PCR inhibition that may occur from excess Wash Buffer.
3.2.3.2 Wait 1 minute to allow the Pipette Tip Filter to thoroughly dry.
The nucleic acid is still bound to the Pipette Tip Filter.
3.2.4 Elute purified maternal and fetal nucleic acids from Pipette Tip
3.2.4.1 Draw Elution Buffer up through Pipette Tip and wait 1 minute to allow Elution Buffer to incubate on the Filter.
3.2.4.2 Pipette liquid into Elution 1 Tube and repeat for a total of 5 cycles.
3.2.4.3 Repeat Steps 3.2.4.1 and 3.2.4.2 with Elution 2 Tube.
3.2.4.4 Spin down tubes and combine sample from Elution Tubes 1 & 2.
3.2.4.5 Measure the total volume contained in Elution Tube and bring the volume up to 450 µl with Elution Buffer A2.
Extracted nucleic acid is now in the Elution Tube.
3.2.4.6 Discard the Pipette Tip.
Purified nucleic acid is now ready for Exclusion and Concentration.
3.3.0 Exclusion of HMW Nucleic Acids
3.3.1 Set-Up:
3.3.1.1 Transfer the eluted sample from step 3.2.4.5 to the 2 ml microcentrifuge tube labeled with the appropriate sample number.
3.3.1.2 Add 495 µl Binding Buffer CN-B2.
3.3.1.3 Vortex sample for 10 seconds and pulse spin.

3.3.2 Selectively bind HMW nucleic acids to Pipette Tip
3.3.2.1 Attach a 1 ml 4 mm Pipette Tip to an electronic pipette.
3.3.2.2 Pipette liquid from Sample Tube for 20 cycles (cycle=aspirate+dispense).
3.3.2.3 Close the Sample Tube and set aside.
DO NOT discard; Sample Tube contains fetal DNA.
3.3.2.4 Retain the Pipette Tip.
The high MW nucleic acid (maternal DNA) is now bound to the Pipette Tip Filter.
3.3.3 Rinse Pipette Tip
3.3.3.1 Pipette liquid in Rinse Tube for 5 cycles.
3.3.3.2 Discard Rinse Tube but retain the Pipette Tip.
The nucleic acid is released from the Filter.
3.4.0 Concentration of LMW nucleic acids
3.4.1 Set-up:
3.4.1.1 Add 575 µl of Binding Buffer CN-B3 to Sample Tube.
3.4.1.2 Vortex Sample Tube for 10 seconds and pulse spin.
3.4.2 Bind LMW nucleic acids
3.4.2.1 Pipette liquid in Sample Tube for 20 cycles.
3.4.2.2 Discard the Sample Tube but retain the Pipette Tip.
The nucleic acid is now bound to the Filter.
3.4.3 Washing LMW nucleic acids
3.4.3.1 Maintain same settings as above on the Rainin Pipette.
3.4.3.2 Pipette liquid in Wash 1 Tube for 1 cycle.
3.4.3.3 Discard Wash 1 Tube but retain Pipette Tip.
3.4.3.4 Repeat steps 3.4.3.2 and 3.4.3.3 with Wash 2 Tube.
The nucleic acid is still bound to the Filter.
3.4.4 Dry
3.4.4.1 With the Pipette Tip in the empty Drying Tube, pass air through the Pipette Tip for 15 cycles. Gently tap the Pipette Tip intermittently if a noticeable amount of Wash Buffer is left.
This step is to avoid PCR inhibition that may occur from excess Wash Buffer.
3.4.4.2 Wait 1 minute to allow the Filter to thoroughly dry.
The nucleic acid is still bound to the Pipette Tip Filter.
3.4.5 Elute
3.4.5.1 Draw liquid in Elution Tube up through Pipette Tip and wait 1 minute to allow elution buffer to incubate on the Filter.
3.4.5.2 Pipette liquid in Elution Tube for a total of 10 cycles.
3.4.5.3 Retain eluted sample in the Elution Tube.
Extracted nucleic acid is now in the Elution Tube.
3.4.5.4 Discard the Pipette tip.
Purified nucleic acid is now ready for PCR amplification or storage at −20° C. (−80° C. for long-term storage).

Figure 7:
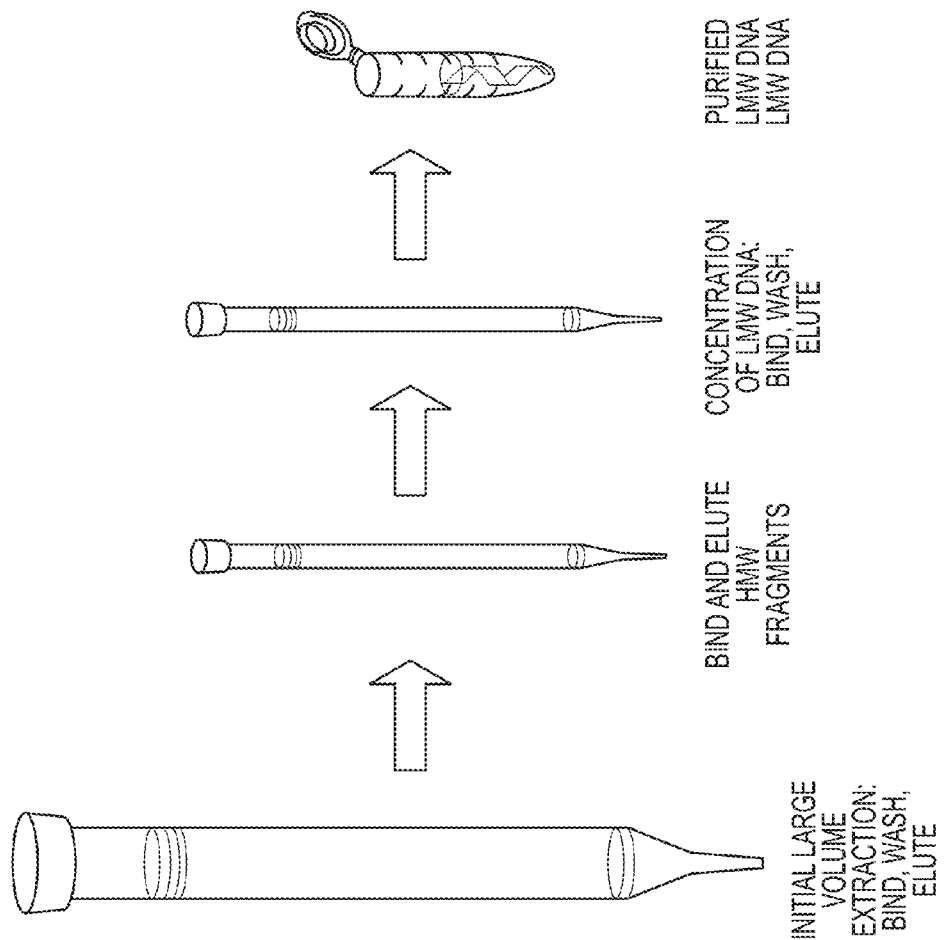
FIG. 7 is a flow diagram showing an embodiment of a process for purifying fetal nucleic acids in accordance with the present application.

The above-described purification procedure is summarized in FIG. 7. In some embodiments, only a single Pipette tip is used in the complete purification procedure (i.e., steps 3.1.0 to 3.4.5.4) to lower the cost of the procedure. Selective binding of fetal and/or maternal DNA to the Pipette tip filter can be achieved with different binding buffer. In some embodiments, the single Pipette tip contains a glass frit filter with two sections of different porosity. In other embodiments, the single Pipette tip contains a sintered glass frit filter with two sections of different porosity. In other embodiments, the single Pipette tip contains two filters of different porosity and the filters are fused to each other. In other embodiments, the single Pipette tip contains two or more filters of different porosity.

In some embodiments, the method described above (i.e., separation of fetal DNA based on size exclusion or enrichment) is used in isolation of other cell-free DNA from samples of cancer patient (for separation of normal DNA from tumor DNA) or samples from transplant patient (for separation of host from donor DNA). The size exclusion/concentration portion of the protocol could also be used in the library preparation protocol prior to performing Next Generation Sequencing. Isolation of small fragments of DNA from large volumes of sample (not necessarily including the enrichment) is also a common application for isolation of infectious diseases from renal samples.

Example 4

Characterization of the Fetal DNA Extraction Procedure

Efficiency of DNA Recovery

Figure 8A:
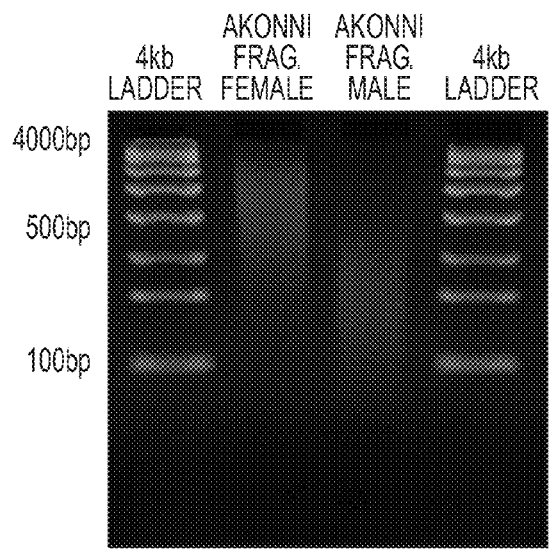
FIG. 8A is a picture of an agarose gel showing female and male genomic DNA fragmented by sonication to simulate lengths found in actual maternal samples (female=maternal DNA, male=fetal DNA).
Figure 8B:
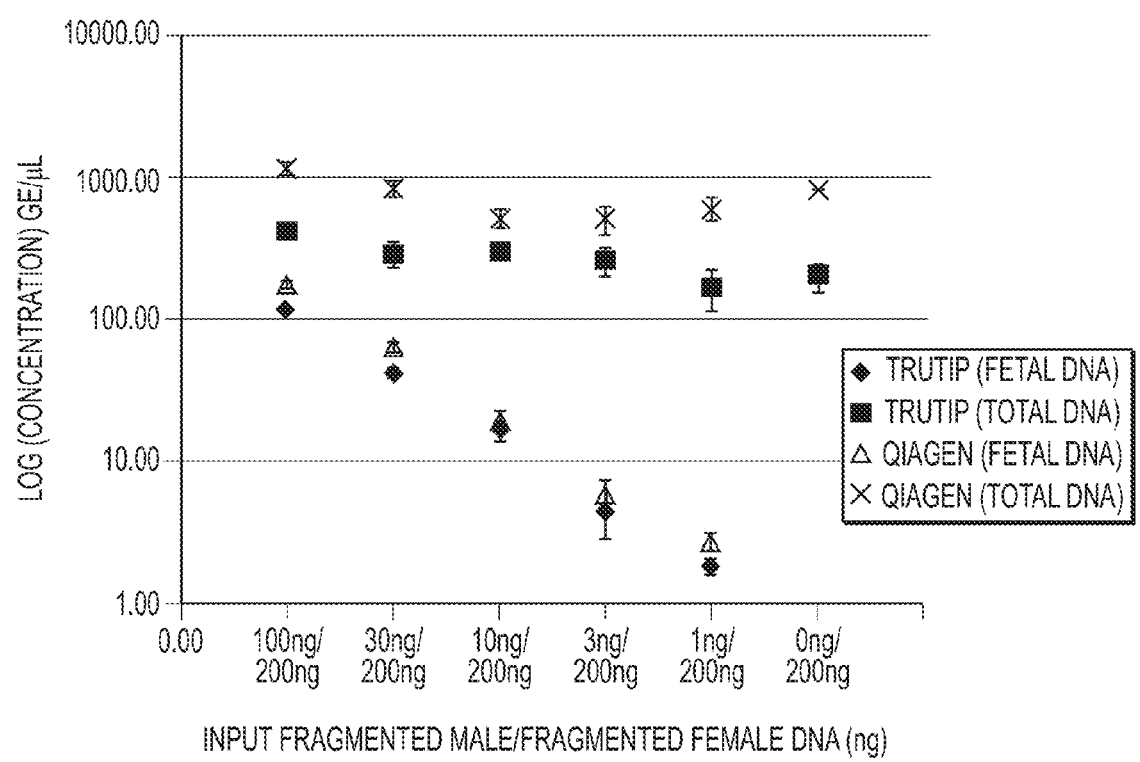
FIG. 8B is a diagram showing recovery of fetal DNA at different dilutions. Real time PCR results from extracted samples containing fragmented male DNA ranging from 100 to 1 ng and total DNA including 200 ng fragmented female DNA per sample for TruTip (solid diamond and solid square) and Qiagen (open triangle and X) respectively, n=3 extractions each with n=3 per sample for PCR. Error bars indicate±one standard deviation.

Full length male and female genomic DNA (Promega) was fragmented using a horn sonicator on the side wall of a PCR tube with glass beads and Sonication time was optimized for female and male DNA to produce desired fragment ranges to develop and demonstrate the ability to discriminate between sizes for the exclusion step of the protocol. The results are shown in FIG. 8A. Male DNA was fragmented to a size range of <600 bp (centered around at about 150 bp) to simulate circulating fetal DNA in a plasma sample. Female DNA was fragmented to a size range of from about 400 bp to about 1200 bp (centered at about 800 bp) to simulate maternal DNA in a plasma sample. Samples containing a mixture of 200 ng fragmented female DNA and various amount of fragmented male DNA (1, 3, 10, 30 and 100 ng) were prepared and extracted with the DNA extraction protocol described in Example 3. FIG. 8B shows the qPCR results of recovery of fragmented male DNA (Chrom Y) DNA and total DNA (Chrom 1). Data shown are the average of three extractions. Each extraction sample was run as a duplicate by qPCR. The results illustrate that effective male DNA recovery is achieved within the tested concentration range and is comparable to the yields using the Qiagen Circulating Nucleic Acids Kit. The lower amount of total DNA recovered for TruTip compared to the Qiagen method demonstrates the effect of the enrichment step in the TruTip protocol.

In another sets of experiments, glass frit filters with different dimensions and matrix porosities were tested for recovery of fetal and maternal DNA. Briefly, 10 ml female plasma spiked with 10 ng male fragmented DNA was processed using glass frit filters with different dimensions and matrix porosities following the procedures described in step 3.2.0 of Example 3 (the extraction step only), the extracted DNA was recovered in 250 ul elution buffer and analyzed by qPCR for fetal (CHY) and total (CH1) DNA. The results are summarized in Table 6.

TABLE 6

| Sample name | Tip Type | CHY (male DNA) | | | | | | CH1 (total DNA) | | | | | |
|---|---|---|---|---|---|---|---|---|---|---|---|---|---|
| | | Cp1 | Conc1 | Cp2 | Conc2 | Avg Cp | Avg Conc | Cp1 | Conc1 | Cp2 | Conc2 | Avg Cp | Avg Conc |
| E1 | 4 mm/8 mm (16-40 um porosity) | 26.93 | 3.51E−01 | 26.82 | 3.77E−01 | 26.92 | 3.55E−01 | 24.99 | 2.59E+00 | 24.93 | 2.68E+00 | 25.00 | 2.57E+00 |

TABLE 6-continued

| Sample name | Tip Type | CHY (male DNA) | | | | | | CH1 (total DNA) | | | | | |
|---|---|---|---|---|---|---|---|---|---|---|---|---|---|
| | | Cp1 | Conc1 | Cp2 | Conc2 | Avg Cp | Avg Conc | Cp1 | Conc1 | Cp2 | Conc2 | Avg Cp | Avg Conc |
| E2 | 4 mm/8 mm (16-40 um porosity) | 26.98 | 3.40E−01 | 26.94 | 3.50E−01 | | | 25.05 | 2.49E+00 | 25.04 | 2.50E+00 | | |
| E3 | 4 mm/7 mm (16-40 um porosity) | 27.57 | 2.34E−01 | 27.63 | 2.25E−01 | 27.19 | 3.08E−01 | 25.77 | 1.60E+00 | 25.85 | 1.53E+00 | 25.34 | 2.18E+00 |
| E4 | 4 mm/7 mm (16-40 um porosity) | 26.79 | 3.84E−01 | 26.78 | 3.87E−01 | | | 24.87 | 2.77E+00 | 24.86 | 2.80E+00 | | |
| E5 | 4 mm/7 mm (dual filter)* | 26.94 | 3.51E−01 | 26.95 | 3.48E−01 | 26.91 | 3.57E−01 | 25.07 | 2.47E+00 | 25.06 | 2.47E+00 | 25.05 | 2.49E+00 |
| E6 | 4 mm/7 mm (dual filter)* | 26.8 | 3.82E−01 | 26.95 | 3.48E−01 | | | 25.02 | 2.54E+00 | 25.06 | 2.48E+00 | | |
| E7 | 4 mm/7 mm (40-60 um porosity) | 28.53 | 1.21E−01 | 28.35 | 1.39E−01 | 28.79 | 1.04E−01 | 26.86 | 8.29E−01 | 26.8 | 8.58E−01 | 26.97 | 7.81E−01 |
| E8 | 4 mm/7 mm (40-60 um porosity) | 29.22 | 7.22E−02 | 29.05 | 8.22E−02 | | | 27.09 | 7.23E−01 | 27.11 | 7.14E−01 | | |

Figure 9:
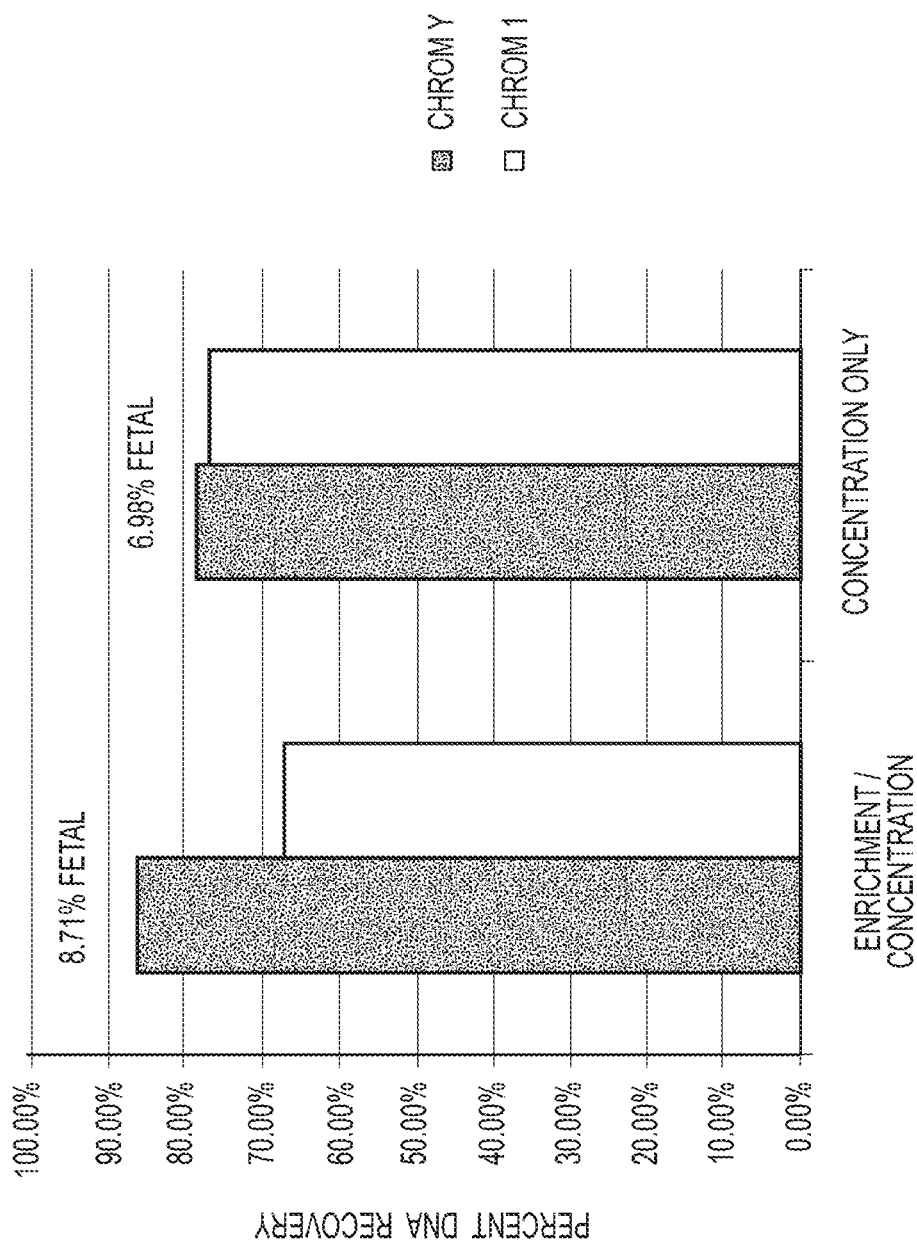
FIG. 9 is a diagram showing fetal DNA (Chrom Y) and total DNA (Chrom 1) recovery with or without the enrichment step of the present application. Four replicates of maternal plasma, 5 ml each. CHY quantifies male fetal DNA and CH1 quantitates total DNA present (fetal and maternal). qPCR was run on the LightCycler 480 system with previously published assays targeting CHY and CH1.

A mixture of fragmented male and female DNA (input) was extracted using the basic protocol of Example 3 with or without step 3.3. As shown in FIG. 9, in the absence of exclusion step 3.3, the concentration step 3.4 is able to recover 80% of the male DNA with slight enrichment compared to the input (~2.4%). When the exclusion step 3.3 is included with the concentration step, results show that there is slightly lower recovery for the male DNA (CHY), but significantly lower female DNA recovery, resulting in an overall increase in % fetal DNA of ~8% in this case (Table 7).

Set-up:

5.1 Turn on the STARplus instrument and computer.

5.2 Open the Hamilton Run Control software.

5.3 Open the Run file provided by Akonni for 8 large volume plasma samples.

5.4 Place labware onto the STARplus deck as shown in FIG. 10.

5.5 Dispense reagents into their corresponding reservoirs according to Table 8:

TABLE 7

| Sample name | CHY (male DNA) | | | | | CH1 (total DNA) | | | | | |
|---|---|---|---|---|---|---|---|---|---|---|---|
| | Avg. Cp | Std. Dev. (CP) | Avg. Conc. (GES/uL) | Avg. Conc. (ng/uL) | % Recovery | Avg. Cp | Std. Dev. (Cp) | Avg. Conc. (GES/uL) | Avg. Conc. (ng/uL) | % Recovery | % Fetal |
| Input | 26.21 | | 5.76E+01 | 3.80E−01 | | 24.07 | | 5.38E+02 | 3.55E+00 | | 10.7% |
| TruTip Exclusion & Conc. (n = 4) | 26.75 | 0.17 | 3.99E+01 | 2.63E−01 | 69.24 | 25.38 | | 2.16E+02 | 1.43E+00 | 40.15 | 18.5% |
| Input | 26.53 | | 4.61E+01 | 3.04E−01 | | 24.52 | | 3.93E+02 | 2.59E+00 | | 11.7% |
| TruTip Conc. Only (n = 4) | 26.78 | 0.20 | 3.90E+01 | 2.57E−01 | 84.62 | 25.04 | 0.23 | 2.77E+02 | 1.83E+00 | 70.54 | 14.1% |

GES = genome equivalents

Example 5

Automated Protocol for Extracting Fetal Nucleic Acids from Large Volume Plasma Samples The Hamilton STARplus instrument was used to develop and demonstrate an automated protocol for extracting freely circulating fetal DNA from 5 ml of maternal plasma. The STARplus system can support two automated pipette channel arms, one with 8×5 ml channels and one with 8×1 ml channels. These arms can operate in parallel for staggered processing in batches of 8 samples each. A 5 ml filter tip may be used for the initial large-volume extraction, and a 1 ml filter tip may be used for size separation and further concentration of the extracted nucleic acid.

TABLE 8

| Reagent | Volume (ml) | Trough Position |
|---|---|---|
| CN-W1 | 17 | 5A |
| CN-W2 | 17 | 5B |
| CN-W2 | 21 | 5C |
| Proteinase K (20 mg ml$^{-1}$) | 5 | 6A |
| EBB | 17 | 6B |
| EBA2 | 5 | 6C |
| CN-W3 | 5 | 6D |
| CN-B2 | 5 | 6E |
| CN-B3 | 5 | 6F |
| CN-L1 | 175 | 7 |
| CN-B1 | 52 | 8 |

5.6 Allow sample to equilibrate to room temperature.

5.7 Place the sample tubes in the Sample Carrier racks (deck position 3 in FIG. 10A). Place Sample 1 in the rear and move sequentially toward the front of the deck.

Automated Program:

Because of the large input sample volume, pre-treatment steps must be performed off of the Hamilton STARplus instrument in a water bath. Steps requiring user intervention within the automated protocol are indicated with an asterisk (*) at the beginning of the sentence, and bold type.

Pre-Treatment:

The sample is incubated with proteinase K and lysis buffer to homogenize the sample and lyse cells to release the DNA.

5.8 Select the PLAY button in the upper left of the Run file window.

5.9 The automated script adds 5 ml plasma, 615 ul proteinase K, and 6.3 ml Lysis Buffer CN-L1 to each 50 ml conical tube, and will then PAUSE.

5.10 *Remove the 50 ml conical tubes from the sample deck, vortex for 30 seconds on high speed, and incubate off-line for 30 min at 60° C. in a water bath or heat block. After the conical tubes are removed from the Hamilton deck, RESUME the automated script to continue dispensing reagents into their respective plates and wells (FIGS. 10B and 10C):

2 ml CN-W1 to every-other well in position 9 column 1
2 ml CN-W2 to every-other well in position 9 column 2
2 ml CN-W4 to every-other well in position 9 column 3
250 µl EA2 to every-other well in position 9 columns 4 and 5.
1 ml EBB to every well in position 10 column 2.
500 µl CN-W3 to every well in position 10 column 3.
500 µl CN-W4 to every well in position 10 column 4.
50 µl EBA2 to every well in position 10 column 5.

Because the 5 ml channels are too wide to use adjacent wells for each sample, the automated program therefore dispenses reagents into every other well of the deep well plate in deck position 9.

After dispensing reagents, the program will PAUSE.

5.11 *After the 30 min, 60° C. incubation, place the 50 ml conical tubes on ice for 5 min.

5.12 *Return 50 ml conical tubes to their original positions within the sample carrier rack at deck position 4, and RESUME the automated script.

5.13 Add 12 ml Binding Buffer CN-B1 to each sample tube and mix 10 times.

Large Volume Extraction:

5 ml filter tips may be used for extracting total DNA from the lysed plasma sample.

5.14 Pick up 5 ml filter tips from position 2 for the large-volume nucleic acid extraction.

5.15 Cycle the sample mixture 15 times in the 50 ml conical tube, starting at the bottom of the tube and moving 3 mm higher after each pipetting cycle. This step binds the total nucleic acid to the binding matrix.

5.16 Move the filter tips to the deep well plates at position 6 column 1, and cycle 1 time in Wash Buffer CN-W1.

5.17 Move the filter tips to position 9 column 2 and cycle 1 time in Wash CN-W2.

5.18 Move the filter tips to position 9 column 3 and cycle 2 times in Wash CN-W4.

5.19 Move the filter tips to position 9 column 4 and cycle 40 times at high speed to dry binding matrix.

5.20 Move the filter tips to position 9 column 5 and cycle 10 times to elute the bound nucleic acids from the 5 ml filter tips. This is large-volume elution #1.

5.21 Move the filter tips to column 6 and repeat the step with the second aliquot of elution buffer. This is large-volume elution #2.

5.22 Transfer elution #2 into position 9 column 5 to combine it with elution #1, and discard the filter tips.

Exclusion and Concentration:

The high molecular weight DNA is removed from the extracted sample, and the remaining DNA is isolated and concentrated.

5.23 Add combined eluant from step 5.22 to position 10 column 1 and mix thoroughly 10 times.

5.24 Pick up 1 ml filter tips from position 13 and cycle 20 times to bind the high molecular weight DNA to the matrix.

5.25 Move the filter tips to position 10 column 2 and cycle 5 times to rinse the tip. The filter tips are retained and placed back in the tip rack at position 13.

5.26 With reagent tips from position 12, add 575 µl of Binding Buffer CN-B3 to the sample in position 10 column 1 and mix 10 times.

5.27 Pick up the filter tips from step 5.25, return to position 10 column 1, and cycle 20 times to bind the remaining DNA from the sample to the 1 ml filter tip.

5.28 Move the filter tips to position 10 column 4 and cycle 1 time in Wash CN-W3 to remove any remaining inhibitors.

5.29 Move the filter tips to position 10 column 5 and cycle 1 time in Wash CN-W4 to rinse residual guanidine from CN-W3.

5.30 Raise the filter tips over position 10 column 5 and cycle air through the tips 35 times to dry the matrix.

5.31 Move the filter tips to position 10 column 6 and cycle 10 times in EBA2 to elute the purified, size-selected and concentrated nucleic acid.

5.32 Discard the filter tips.

5.33 Transfer the eluted sample from column 6 to 1.5 ml tubes in position 11. Extracted samples are ready for storage or downstream processing.

Table 9 provides a listing of the reagents and equipment used in Example 5.

TABLE 9

| Reagent/Material | Company | Catalog Number |
| --- | --- | --- |
| TruTip R + D Circulating DNA Extraction Kit (Hamilton TruTips ®) | Akonni Biosystems | |
| 100% ethanol | Sigma-Aldrich | 459828-1L |
| Isopropanol | Acros Organics/Fisher Scientific | AC327270010 |
| Filtered 4 ml Tips | Hamilton | 184022 |
| Unfiltered 1 ml Tips | Hamilton | 235939 |
| 96-Deep Well Plates | USA Scientific | 1896-2800 |

TABLE 9-continued

| | Company | Catalog Number |
|---|---|---|
| 50 ml Conical Tubes | Corning/Fisher-Scientific | 05-526B |
| 50 ml Reagent Troughs | Hamilton | |
| 120 ml Reagent Troughs | Hamilton | 182703 |
| Large Volume 96-Pos Reagent Troughs | Fisher Scientific | 14-222-412 |
| Equipment | | |
| Hamilton STARplus System | Hamilton | |
| Tip Carriers | Hamilton | 182085 |
| 50 ml Tube Carriers | Hamilton | 182245 |
| 24 Position Sample Carriers | Hamilton | |
| 32 Position Sample Carrier | Hamilton | 173410 |
| Multiflex Carrier (7 Track wide) | Hamilton | Position 1: CPAC or HHS with Round bottom plate adapter |
| | Hamilton | Position 2: MFX_Rgt Module (PN 188047) with track (7 à 6) adapter |
| | Hamilton | Position 3: MFX_DWP Module (PN 188042) with track (7 à 6) adapter |
| | Hamilton | Position 4: MFX_DWP Module (PN 188042) with track (7 à 6) adapter |

Figure 11A:
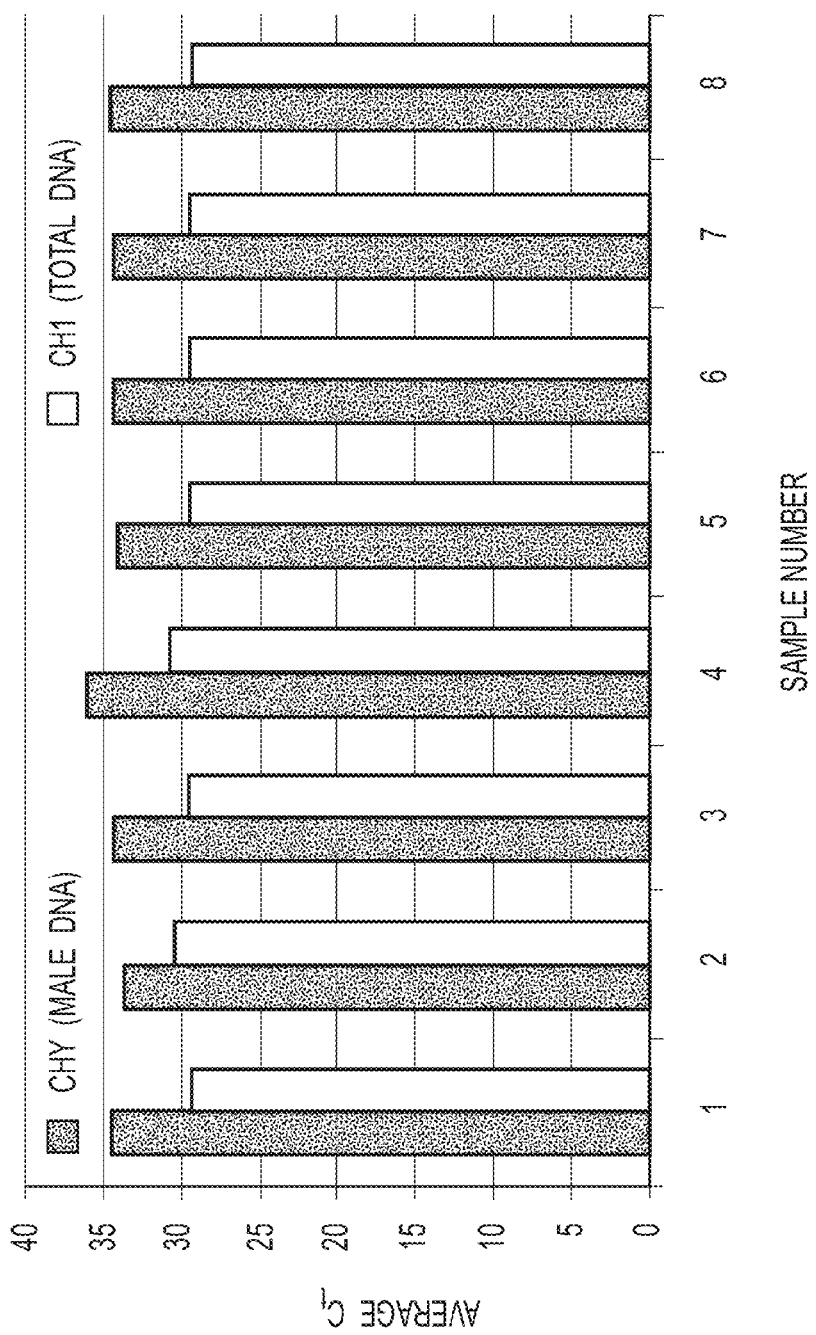
FIG. 11A depicts qPCR results from eight replicate samples of a pooled maternal plasma sample processed with the large-volume filter tip procedure. The full protocol (including off-line proteinase K pre-treatment) is finished in approximately 2 hours. The average $C_t$ values over all replicates were 34.58±0.66 and 29.76±0.50 for fetal male (CHY) and total (CH1) DNA, respectively, which demonstrates excellent repeatability of the automated extraction method. The concentration of fetal DNA within the total DNA pool (in genome equivalents), was calculated based on fit point analysis comparison to standards, with the resulting average % fetal DNA across all samples of 2.8%. The actual % fetal DNA for this sample is unknown because the samples were pooled before performing the extraction.

Representative Results:

Real-time results from eight replicate samples of a pooled maternal plasma sample processed with the large-volume filter tip procedure are shown in FIG. 11A. The full protocol (including off-line proteinase K pre-treatment) is finished in approximately 2 hours. The average $C_t$ values over all replicates were 34.58±0.66 and 29.76±0.50 for fetal male (CHY) and total (CH1) DNA, respectively, which demonstrates excellent repeatability of the automated extraction method. The concentration of fetal DNA within the total DNA pool (in genome equivalents), was calculated based on fit point analysis comparison to standards, with the resulting average % fetal DNA across all samples of 2.8%. The actual % fetal DNA for this sample is unknown because the samples were pooled before performing the extraction.

Figure 11B:
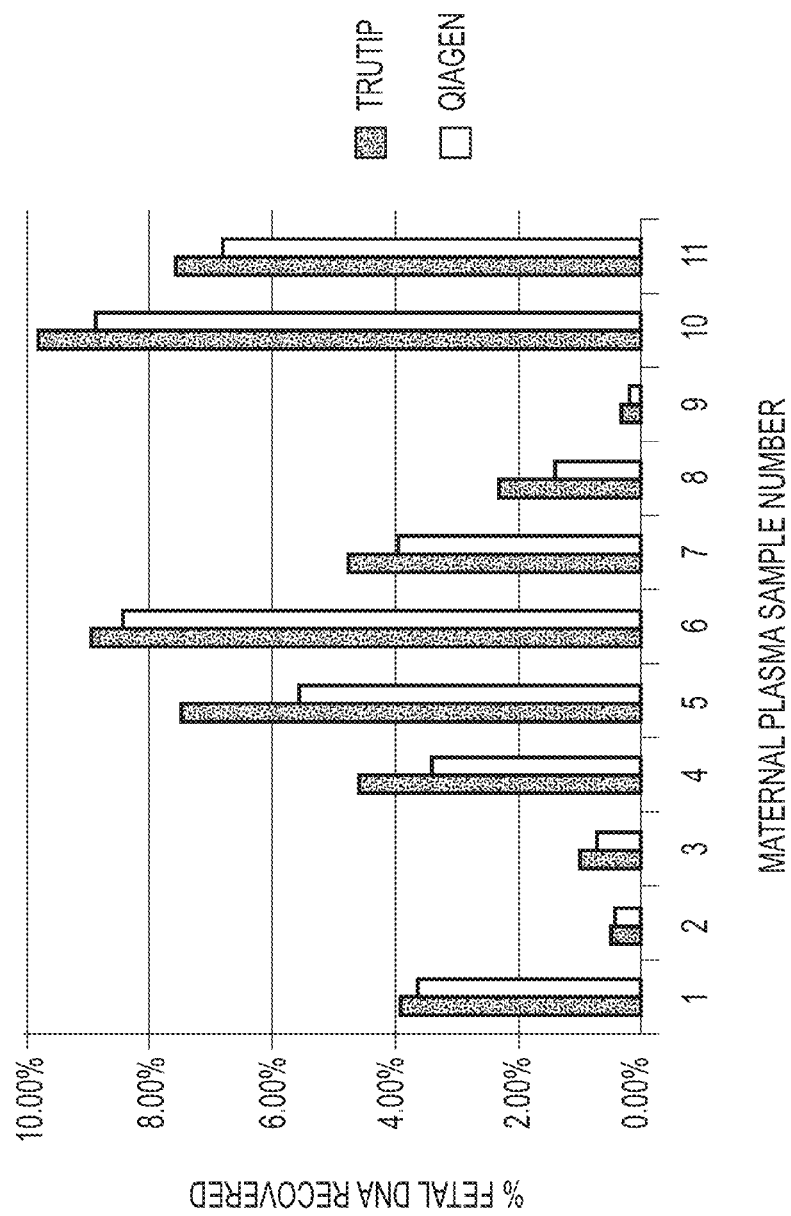
FIG. 11B shows a comparison of percent fetal DNA recovered from 11 unique duplicate maternal plasma samples using an automated system employing Akonni TruTip® filters in accordance with the above-described extraction procedures (left column/pairs) and Qiagen's manual Circulating Nucleic Acid Kit (right column/pairs).

FIG. 11B shows a comparison of percent fetal DNA recovered from 11 unique duplicate maternal plasma samples using an automated system employing Akonni TruTip® filters in accordance with the above-described extraction procedures (left column/pairs) and Qiagen's manual Circulating Nucleic Acid Kit (right column/pairs).

Without being bound to any particular theory or action, the present invention meets the needs described above by implementing a rigid, self-supporting matrix structure that is relatively thick for high binding capacity, contains relatively large porosities for low fluid impedance, faster flow rates, and higher tolerance to particles in clinical and environmental samples, and consists of no loose material (e.g., silica gel, diatomaceous earth, glass beads).

The binding matrix and tip format provides numerous advantages not realized in current technologies including: i) high-surface area for increased extraction efficiency and concentration, ii) large porosity for large sample volumes and dirty samples, iii) simple concept obviating the need for a centrifuge or vacuum manifold; and iv) compatibility of extracted products with any downstream amplification detection system. The system described herein avoids the use of flimsy, delicate materials (e.g., fiber filters, membrane filters, silicon microstructures) so as to provide rugged operation and simplified manufacturing that is well characterized and easily scaled-up for higher throughput processing on a robotics liquid handing system.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A method for separating and isolating fetal nucleic acids from maternal nucleic acids in a plasma sample, comprising:
    (a) flowing a plasma sample comprising fetal nucleic acids and maternal nucleic acids through a first filter, under conditions that allow specific binding of the fetal and maternal nucleic acids to the first filter;
    (b) eluting bound fetal and maternal nucleic acids from the first filter to form a concentrated nucleic acid sample comprising fetal nucleic acids and maternal nucleic acids;
    (c) flowing the concentrated nucleic acid sample through a second filter, under conditions that allow the maternal nucleic acids to bind to the second filter and the fetal nucleic acids to flow through the second filter; and
    (d) collecting the flow-through fraction from the second filter, wherein the flow-through fraction from the second filter contains fetal nucleic acids,
    wherein the conditions that allow specific binding of the fetal and maternal nucleic acids to the first filter in step (a) comprise forming a first binding mixture that comprises the plasma sample, an aliphatic alcohol in a range between about 17-25% (v/v) and a chaotropic salt in a concentration range between about 0.5 M to about 4.0 M.

2. The method of claim 1, wherein the conditions for binding the maternal nucleic acids to the second filter in step (c) comprise forming a second binding mixture that comprises the concentrated nucleic acid sample, an aliphatic alcohol in a range between about 0-10% (v/v) and a chaotropic salt in a concentration range between about 1 M to about 4.0 M.

3. The method of claim 1, further comprising the steps of:
(e2) flowing the flow-through fraction from the second filter through a third filter under conditions that allow binding of the fetal nucleic acids to the third filter; and
(f2) eluting bound fetal nucleic acids from the third filter.

4. The method of claim 1, wherein one or both of the first and second filter comprises a glass fit comprising a first section having a first pore size and second section having a second pore size, wherein the first pore size is different from the second pore size.

5. The method of claim 1, further comprising the steps of:
(e1) eluting bound maternal nucleic acids from the second filter to produce a regenerated second filter;
(f1) flowing the flow-through fraction from the second filter through the regenerated second filter under conditions that allow binding of fetal nucleic acids to the second filter; and
(h1) eluting bound fetal nucleic acids from the second filter in step (f1).

6. The method of claim 5, wherein the conditions for binding the fetal nucleic acids to the second filter in step (f1) comprise forming a third binding mixture that comprises the flow-through fraction from the second glass frit filter, an aliphatic alcohol in a range between about 10-25% (v/v) and a chaotropic salt in a concentration range between about 1 M to about 5.0 M.

7. The method of claim 1, wherein the first and second filters are self-supporting glass fits.

8. The method of claim 7, wherein the glass fits are sintered glass frits.

9. The method of claim 7, wherein the first glass frit filter has a pore size of 16-40 micron and the second glass frit filter has a pore size of 4-5.5 micron.

* * * * *